US010195157B2

(12) United States Patent
Topolkaraev et al.

(10) Patent No.: US 10,195,157 B2
(45) Date of Patent: Feb. 5, 2019

(54) DELIVERY SYSTEM FOR ACTIVE AGENTS

(71) Applicant: Kimberly-Clark Worldwide, Inc., Neenah, WI (US)

(72) Inventors: Vasily A. Topolkaraev, Appleton, WI (US); Neil T. Scholl, Neenah, WI (US); Ryan J. McEneany, Appleton, WI (US); Thomas A. Eby, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/909,752

(22) PCT Filed: Jul. 9, 2014

(86) PCT No.: PCT/IB2014/062975
§ 371 (c)(1),
(2) Date: Feb. 3, 2016

(87) PCT Pub. No.: WO2015/019211
PCT Pub. Date: Feb. 12, 2015

(65) Prior Publication Data
US 2016/0193157 A1    Jul. 7, 2016

Related U.S. Application Data

(60) Provisional application No. 61/863,938, filed on Aug. 9, 2013.

(51) Int. Cl.
| *A61K 9/16* | (2006.01) |
| *A61K 9/70* | (2006.01) |
| *A61K 9/50* | (2006.01) |
| *A61L 15/44* | (2006.01) |
| *A61L 15/46* | (2006.01) |
| *C08J 5/18* | (2006.01) |
| *C08L 67/04* | (2006.01) |
| *A61L 15/42* | (2006.01) |
| *A61K 9/00* | (2006.01) |

(52) U.S. Cl.
CPC .............. *A61K 9/70* (2013.01); *A61K 9/1647* (2013.01); *A61K 9/1694* (2013.01); *A61K 9/5015* (2013.01); *A61K 9/7007* (2013.01); *A61L 15/425* (2013.01); *A61L 15/44* (2013.01); *A61L 15/46* (2013.01); *C08J 5/18* (2013.01); *C08L 67/04* (2013.01); *A61K 9/0092* (2013.01); *A61L 2400/12* (2013.01)

(58) Field of Classification Search
None
See application file for complete search history.

(56) References Cited

U.S. PATENT DOCUMENTS

| 3,423,255 A | 1/1969 | Joyce |
|---|---|---|
| 3,802,817 A | 4/1974 | Matsuki et al. |
| 3,855,046 A | 12/1974 | Hansen et al. |
| 4,041,203 A | 8/1977 | Brock et al. |
| 4,100,324 A | 7/1978 | Anderson et al. |
| 4,282,735 A | 8/1981 | Break |
| 4,374,888 A | 2/1983 | Bornslaeger |
| 4,557,132 A | 12/1985 | Break |
| 4,698,372 A | 10/1987 | Moss |
| 4,741,944 A | 5/1988 | Jackson et al. |
| 4,766,029 A | 8/1988 | Brock et al. |
| 4,797,468 A | 1/1989 | De Vries |
| 4,937,299 A | 6/1990 | Ewen et al. |
| D315,990 S | 4/1991 | Blenke et al. |
| 5,030,404 A | 7/1991 | Bonnebat et al. |
| 5,169,706 A | 12/1992 | Collier, IV et al. |
| 5,179,164 A | 1/1993 | Lausberg et al. |
| 5,213,881 A | 5/1993 | Timmons et al. |
| 5,218,071 A | 6/1993 | Tsutsui et al. |
| 5,272,236 A | 12/1993 | Lai et al. |
| 5,278,272 A | 1/1994 | Lai et al. |
| 5,284,703 A | 2/1994 | Everhart et al. |
| 5,322,728 A | 6/1994 | Davey et al. |
| 5,350,624 A | 9/1994 | Georger et al. |
| D358,035 S | 5/1995 | Zander et al. |
| 5,464,688 A | 11/1995 | Timmons et al. |
| 5,470,944 A | 11/1995 | Bonsignore |
| 5,472,775 A | 12/1995 | Obijeski et al. |
| 5,503,785 A | 4/1996 | Crump et al. |
| 5,539,056 A | 7/1996 | Yang et al. |

(Continued)

FOREIGN PATENT DOCUMENTS

WO    WO 2012/109144 A1    8/2012

OTHER PUBLICATIONS

Brad Jones et al., Nanoporous Materials Derived from Polymeric Bicontinuous Microemulsions, Chemistry of Materials Communication, 3 pages, Jan. 6, 2010, vol. 22, pp. 1279-1281.
E.K. Patel et al., Nanosponge and Micro Sponges: A Novel Drug Delivery System, International Journal of Research in Pharmacy and Chemistry, 8 pages, 2012, vol. 2, No. 2, pp. 237-244.
Zhiwei Xie, et al., Electrospun Poly (D,L—lactide) Fibers for Drug Delivery: The Influence of Cosolvent and the Mechanism of Drug Release, Journal of Applied Polymer Science, 8 pages, 2010, vol. 22, pp. 1279-1281.
International Search Report and Written Opinion for PCT/IB2014/062976, dated Dec. 8, 2014, 14 pages.
Shields et al., Fibrillar polymer-polymer composites: morphology, properties and applications, Journal of Materials Science, Kluwer Academic Publishers, vol. 43, No. 20, Sep. 20, 2008, pp. 6758-6770.

*Primary Examiner* — Brian Gulledge
(74) *Attorney, Agent, or Firm* — Dority & Manning, P.A.

(57) ABSTRACT

A delivery system containing an active agent within a polymeric material formed from a thermoplastic composition is provided. Through selective control over the particular nature of the thermoplastic composition, as well as the manner in which it is formed, the present inventors have discovered that a porous network can be created that contains a plurality of micropores and nanopores. The ability to create such a multimodal pore size distribution can allow the delivery rate of an active agent to be tailored for a particular use.

20 Claims, 10 Drawing Sheets

(56) References Cited

U.S. PATENT DOCUMENTS

| | | |
|---|---|---|
| 5,540,332 A | 7/1996 | Kopacz et al. |
| 5,571,619 A | 11/1996 | McAlpin et al. |
| 5,596,052 A | 1/1997 | Resconi et al. |
| 5,620,779 A | 4/1997 | Levy et al. |
| 5,667,635 A | 9/1997 | Win et al. |
| D384,508 S | 10/1997 | Zander et al. |
| D384,819 S | 10/1997 | Zander et al. |
| D390,708 S | 2/1998 | Brown |
| 5,764,521 A | 6/1998 | Batchelder et al. |
| 5,770,682 A | 6/1998 | Ohara et al. |
| 5,814,673 A | 9/1998 | Khait |
| 5,821,327 A | 10/1998 | Oota et al. |
| 5,880,254 A | 3/1999 | Ohara et al. |
| 5,888,524 A | 3/1999 | Cole |
| 5,962,112 A | 10/1999 | Haynes et al. |
| 6,004,124 A | 12/1999 | Swanson et al. |
| D418,305 S | 1/2000 | Zander et al. |
| 6,028,018 A | 2/2000 | Amundson et al. |
| 6,070,107 A | 5/2000 | Lombardi et al. |
| D428,267 S | 7/2000 | Romano, III et al. |
| 6,090,325 A | 7/2000 | Wheat et al. |
| 6,093,665 A | 7/2000 | Sayovitz et al. |
| 6,228,923 B1 | 5/2001 | Lombardi et al. |
| 6,326,458 B1 | 12/2001 | Gruber et al. |
| 6,337,198 B1 | 1/2002 | Levene et al. |
| 6,348,258 B1 * | 2/2002 | Topolkaraev ......... B29C 55/005 428/317.9 |
| 6,389,864 B1 | 5/2002 | Chubb et al. |
| 6,431,477 B1 | 8/2002 | Pallmann |
| 6,440,437 B1 | 8/2002 | Krzysik et al. |
| 6,479,003 B1 | 11/2002 | Furgiuele et al. |
| 6,494,390 B1 | 12/2002 | Khait et al. |
| 6,500,563 B1 | 12/2002 | Datta et al. |
| 6,582,810 B2 | 6/2003 | Heffelfinger |
| 6,790,403 B1 | 9/2004 | Priedeman, Jr. et al. |
| 6,818,173 B1 | 11/2004 | Khait |
| 6,923,634 B2 | 8/2005 | Swanson et al. |
| 7,097,904 B2 | 8/2006 | Ochi et al. |
| 7,122,246 B2 | 10/2006 | Comb et al. |
| 7,223,359 B2 | 5/2007 | Torkelson et al. |
| 7,445,735 B2 | 11/2008 | Miller et al. |
| 7,510,133 B2 | 3/2009 | Pallmann |
| 7,604,470 B2 | 10/2009 | LaBossiere et al. |
| 7,625,200 B2 | 12/2009 | Leavitt |
| 7,754,807 B2 | 7/2010 | Priedeman, Jr. et al. |
| 7,891,964 B2 | 2/2011 | Skubic et al. |
| 7,910,041 B1 | 3/2011 | Priedeman, Jr. |
| 7,914,891 B2 | 3/2011 | Amundson et al. |
| 8,334,327 B2 | 12/2012 | Kaufman et al. |
| 8,394,306 B2 | 3/2013 | Nishida et al. |
| 8,512,024 B2 | 8/2013 | Pax |
| 8,684,739 B2 | 4/2014 | Steffier et al. |
| 8,759,446 B2 | 6/2014 | Li et al. |
| 8,936,740 B2 | 1/2015 | Topolkaraev et al. |
| 2002/0122828 A1 | 9/2002 | Liu |
| 2003/0113528 A1 | 6/2003 | Moya |
| 2004/0002273 A1 | 1/2004 | Fitting et al. |
| 2004/0241207 A1 * | 12/2004 | Chauhan ............... A61K 9/0048 424/429 |
| 2008/0291391 A1 * | 11/2008 | Meyers .................... G02C 7/04 351/159.34 |
| 2010/0068484 A1 * | 3/2010 | Kaufman ................ B32B 27/20 428/212 |
| 2011/0212179 A1 | 9/2011 | Liu |
| 2012/0040582 A1 | 2/2012 | Topolkaraev et al. |
| 2012/0164905 A1 | 6/2012 | Topolkaraev et al. |
| 2012/0231242 A1 | 9/2012 | Boyer et al. |

* cited by examiner

DELIVERY SYSTEM FOR ACTIVE AGENTS

RELATED APPLICATIONS

The present application is the national stage entry of International Patent Application No. PCT/IB2017/062975 having a filing date of Jul. 9, 2014, which claims priority to U.S. provisional application Ser. No. 61/863,938, filed on Aug. 9, 2013, which are incorporated herein in their entirety by reference thereto.

BACKGROUND OF THE INVENTION

Polymeric materials are routinely to deliver active agents, such as emollients, fragrances, sunscreens, insect repellants, antimicrobial agents, anti-inflammatory agents, drug compounds, etc. For example, fabrics have been developed in which the active agent is impregnated within the interstices of the fibers. The delivery mechanism for such fabrics is generally through the addition of a liquid or by applying pressure. To help control the rate of delivery, the active agents are often encapsulated. For instance, the active agent can be encapsulated within a pocket or sandwiched between multiple layers of the material. While providing some degree of control, such "macro-encapsulation" techniques are generally not capable of sustaining a controlled release profile over an extended period of time. In response to these difficulties, "micro-encapsulation" techniques have also been employed in which the active agent is suspended within the core of a coating material. U.S. Pat. No. 7,914,891 to Amundson, et al., for instance, describes one such microencapsulation system for a dry wipe. Unfortunately, one of the common problems with micro-encapsulation systems is that they generally require the use of complex and costly processing steps (e.g., crosslinking, emulsification, etc.). Another problem is that they often require the use of liquids, solvents or other diluents, which limits their applicability when active release on demand is required.

As such, a need currently exists for an improved delivery system that is capable of controllably releasing an active agent.

SUMMARY OF THE INVENTION

In accordance with one embodiment of the present invention, a delivery system is disclosed that comprises an active agent that is contained within a polymeric material. The polymeric material is formed from a thermoplastic composition containing a continuous phase that includes a matrix polymer. A microinclusion additive and nanoinclusion additive are dispersed within the continuous phase in the form of discrete domains.

In accordance with another embodiment of the present invention, a method for forming a delivery system for an active agent is disclosed. The method comprises melt blending a matrix polymer, microinclusion additive, nanoinclusion additive, and active agent to form a thermoplastic composition that contains a continuous phase that includes the matrix polymer and within which is dispersed discrete domains of the microinclusion additive and the nanoinclusion additive; forming a polymeric material from the thermoplastic composition; and straining the polymeric material to achieve a porous network that contains a plurality of nanopores and micropores.

In accordance with yet another embodiment of the present invention, a method for forming a delivery system for an active agent is disclosed. The method comprises melt blending a matrix polymer, microinclusion additive, and nanoinclusion additive to form a thermoplastic composition that contains a continuous phase that includes the matrix polymer and within which is dispersed discrete domains of the microinclusion additive and the nanoinclusion additive; forming a polymeric material from the thermoplastic composition; straining the polymeric material to achieve a porous network that contains a plurality of nanopores and micropores; and contacting the polymeric material with the active agent before, during, and/or after straining.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
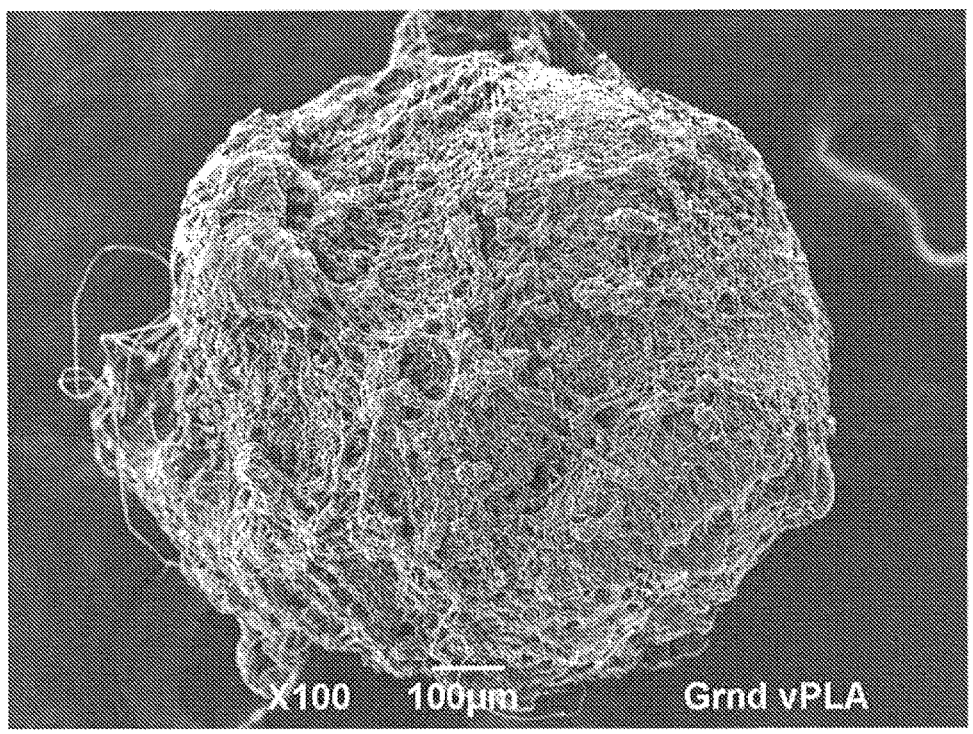
FIGS. 1-2 are SEM microphotographs of the particles of Example 1, where the particles are shown at 100× in FIG. 1 and at 1000× in FIG. 2.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a delivery system that contains an active agent within a polymeric material (e.g., fibrous web, film, particles, etc.) formed from a thermoplastic composition. Through selective control over the particular nature of the thermoplastic composition, as well as the manner in which it is formed, the present inventors have discovered that a porous network can be created that contains a plurality of micropores and nanopores. The ability to create such a multimodal pore size distribution can allow the delivery rate of an active agent to be tailored for a particular use. For example, the flow rate of the active agent tends to be greater through the micropores than the nanopores. Thus, the presence of different classes of pore sizes can help to create a release profile in which a portion of the active agent can be released relatively quickly through the micropores, while another portion of the agent can pass more slowly through the nanopores so that it is delivered over an extended period of time. However, the porous network is not simply a combination of different types of pores. Instead, due to its high degree of complexity and total pore volume, the porous network can form a tortuous pathway that even further enhances the ability to controllably deliver the active agent over an extended period of time.

A particular benefit of the present invention is that the unique porous network described above can be formed without the need for complex microencapsulation techniques traditionally employed to controllably release active agents. Instead, the porous network can be achieved through a monolithic polymeric material, which is simply strained to a certain degree to achieve the desired porous network structure. More particularly, the thermoplastic composition used to form the polymeric material contains microinclusion and nanoinclusion additives dispersed within a continuous phase that includes a matrix polymer. The additives are generally selected so that they are partially incompatible (e.g., different modulus of elasticity) with the matrix polymer. In this manner, the microinclusion and nanoinclusion additives can become dispersed within the continuous phase as discrete micro-scale and nano-scale phase domains, respectively. When subjected to a deformational strain, stress intensification areas can be created at and around the domains, the location of which are dependent upon the particular nature of the additives. When the inclusion additives have a higher modulus than the matrix polymer, for instance, the maximum stress intensification areas are located at the pole of the domains and aligned in the direction of applied stress. The stress intensification areas created by the microinclusion additive can overlap those created by the nanoinclusion additive. In this manner, a dramatic increase in local stresses (i.e., stress amplification) can occur at and around the inclusion boundaries, with the smaller nanoinclusion additives located in the stress intensification areas of the microinclusion additive exhibiting the largest stress amplification. The present inventors have discovered that this stress amplification phenomenon can initiate a controlled and cascading process of debonding and pore formation at or around the inclusion additives, beginning with the smaller nanoinclusion domains exhibiting the larges stress amplification and propagating to the larger microinclusion domains as externally applied stress increases. In addition, because the pores are located adjacent to the discrete domains, a bridge can be formed between the boundaries of the pores that act as internal structural hinges to help prevent the pores from collapsing.

The cascading manner in which pore formation can be initiated allows for the formation of a porous network with the desired multimodal distribution. For instance, a plurality of micropores may be formed at and/or around the microinclusion domains that have an average cross-sectional dimension (e.g., width or diameter) of from about 0.5 to about 30 micrometers, in some embodiments from about 1 to about 20 micrometers, and in some embodiments, from about 2 micrometers to about 15 micrometers. In addition, a plurality of nanopores may be formed at and/or around the second domains that have an average cross-sectional dimension (e.g., width or diameter) of from about 1 to about 500 nanometers, in some embodiments from about 2 to about 450 nanometers, and in some embodiments, from about 5 to about 400 nanometers. It should be understood that multiple subtypes of pores may exist within the general ranges noted above. In certain embodiments, for instance, first nanopores may be formed that have an average cross-sectional dimension of from about 50 to about 500 nanometers, in some embodiments from about 60 to about 450 nanometers, and in some embodiments, from about 100 to about 400 nanometers, while second nanopores may be formed that have an average cross-sectional dimension of from about 1 to about 50 nanometers, in some embodiments from about 2 to about 45 nanometers, and in some embodiments from about 5 to about 40 nanometers.

The micropores and/or nanopores may have any regular or irregular shape, such as spherical, elongated, etc., and may also have an aspect ratio (the ratio of the axial dimension to the cross-sectional dimension) of from about 1 to about 30, in some embodiments from about 1.1 to about 15, and in some embodiments, from about 1.2 to about 5. The average percent volume occupied by the micropores and nanopores within a given unit volume of the material may also be from about 15% to about 80% per $cm^3$, in some embodiments from about 20% to about 70%, and in some embodiments, from about 30% to about 60% per cubic centimeter of the material. In certain cases, nanopores can be present in a relatively high amount. For example, the nanopores may constitute from about 15 vol. % to about 99 vol. %, in some embodiments from about 20 vol. % to 95 vol. %, and in some embodiments, from about 40 vol. % to about 90 vol. % of the total pore volume in the polymeric material. Likewise, the micropores may constitute from about 1 vol. % to about 85 vol. %, in some embodiments from about 5 vol. % to 80 vol. %, and in some embodiments, from about 10 vol. % to about 60 vol. % of the total pore volume in the polymeric material.

The pores (e.g., micropores, nanopores, or both) can also be distributed in a substantially homogeneous fashion throughout the material. For example, the pores may be distributed in columns that are oriented in a direction generally perpendicular to the direction in which a stress is applied. These columns may be generally parallel to each other across the width of the material. Without intending to be limited by theory, it is believed that the presence of such a homogeneously distributed porous network can even further enhance the ability to controllably release the active agent.

In addition to forming a porous network, straining can also significantly increase the axial dimension of the micro-scale domains so that they have a generally linear, elongated shape, which can enhance the mechanical properties and stability of the resulting polymeric material. For example, the elongated micro-scale domains may have an axial dimension that is about 10% or more, in some embodiments from about 20% to about 500%, and in some embodiments, from about 50% to about 250% greater than the axial dimension of the domains prior to straining. The average axial dimension after straining may, for instance, range from about 0.5 to about 250 micrometers, in some embodiments from about 1 to about 100 micrometers, in some embodiments from about 2 to about 50 micrometers, and in some embodiments, from about 5 to about 25 micrometers. The micro-scale domains may also be relatively thin and thus have a small cross-sectional dimension. For instance, the cross-sectional dimension may be from about 0.05 to about 50 micrometers, in some embodiments from about 0.2 to about 10 micrometers, and in some embodiments, from 0.5 to about 5 micrometers. This may result in an aspect ratio for the micro-scale domains (the ratio of the axial dimension to the cross-sectional dimension) of from about 2 to about 150, in some embodiments from about 3 to about 100, and in some embodiments, from about 4 to about 50.

Various embodiments of the present invention will now be described in more detail.

I. Thermoplastic Composition

A. Matrix Polymer

As indicated above, the thermoplastic composition contains a continuous phase within which the microinclusion and nanoinclusion additives are dispersed. The continuous phase contains one or more matrix polymers, which typically constitute from about 60 wt. % to about 99 wt. %, in some embodiments from about 75 wt. % to about 98 wt. %, and in some embodiments, from about 80 wt. % to about 95 wt. % of the thermoplastic composition. The nature of the matrix polymer(s) used to form the continuous phase is not critical and any suitable polymer may generally be employed, such as polyesters, polyolefins, styrenic polymers, polyamides, etc. In certain embodiments, for example, polyesters may be employed in the composition to form the polymer matrix. Any of a variety of polyesters may generally be employed, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aliphatic-aromatic copolyesters (e.g., polybutylene adipate terephthalate, polyethylene adipate terephthalate, polyethylene adipate isophthalate, polybutylene adipate isophthalate, etc.); aromatic polyesters (e.g., polyethylene terephthalate, polybutylene terephthalate, etc.); and so forth.

In certain cases, the thermoplastic composition may contain at least one polyester that is rigid in nature and thus has a relatively high glass transition temperature. For example, the glass transition temperature ("$T_g$") may be about 0° C. or more, in some embodiments from about 5° C. to about 100° C., in some embodiments from about 30° C. to about 80° C., and in some embodiments, from about 50° C. to about 75° C. The polyester may also have a melting temperature of from about 140° C. to about 300° C., in some embodiments from about 150° C. to about 250° C., and in some embodiments, from about 160° C. to about 220° C. The melting temperature may be determined using differential scanning calorimetry ("DSC") in accordance with ASTM D-3417. The glass transition temperature may be determined by dynamic mechanical analysis in accordance with ASTM E1640-09.

One particularly suitable rigid polyester is polylactic acid, which may generally be derived from monomer units of any isomer of lactic acid, such as levorotory-lactic acid ("L-lactic acid"), dextrorotatory-lactic acid ("D-lactic acid"), meso-lactic acid, or mixtures thereof. Monomer units may also be formed from anhydrides of any isomer of lactic acid, including L-lactide, D-lactide, meso-lactide, or mixtures thereof. Cyclic dimers of such lactic acids and/or lactides may also be employed. Any known polymerization method, such as polycondensation or ring-opening polymerization, may be used to polymerize lactic acid. A small amount of a chain-extending agent (e.g., a diisocyanate compound, an epoxy compound or an acid anhydride) may also be employed. The polylactic acid may be a homopolymer or a copolymer, such as one that contains monomer units derived from L-lactic acid and monomer units derived from D-lactic acid. Although not required, the rate of content of one of the monomer unit derived from L-lactic acid and the monomer unit derived from D-lactic acid is preferably about 85 mole % or more, in some embodiments about 90 mole % or more, and in some embodiments, about 95 mole % or more. Multiple polylactic acids, each having a different ratio between the monomer unit derived from L-lactic acid and the monomer unit derived from D-lactic acid, may be blended at an arbitrary percentage. Of course, polylactic acid may also be blended with other types of polymers (e.g., polyolefins, polyesters, etc.).

In one particular embodiment, the polylactic acid has the following general structure:

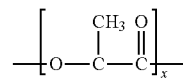

One specific example of a suitable polylactic acid polymer that may be used in the present invention is commercially available from Biomer, Inc. of Krailling, Germany) under the name BIOMER™ L9000. Other suitable polylactic acid polymers are commercially available from Natureworks LLC of Minnetonka, Minn. (NATUREWORKS®) or Mitsui Chemical (LACEA™). Still other suitable polylactic acids may be described in U.S. Pat. Nos. 4,797,468; 5,470,944; 5,770,682; 5,821,327; 5,880,254; and 6,326,458.

The polylactic acid typically has a number average molecular weight ("$M_n$") ranging from about 40,000 to about 180,000 grams per mole, in some embodiments from about 50,000 to about 160,000 grams per mole, and in some embodiments, from about 80,000 to about 120,000 grams per mole. Likewise, the polymer also typically has a weight average molecular weight ("$M_w$") ranging from about 80,000 to about 250,000 grams per mole, in some embodiments from about 100,000 to about 200,000 grams per mole, and in some embodiments, from about 110,000 to about 160,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art.

The polylactic acid may also have an apparent viscosity of from about 50 to about 600 Pascal seconds (Pa·s), in some embodiments from about 100 to about 500 Pa·s, and in some embodiments, from about 200 to about 400 Pa·s, as determined at a temperature of 190° C. and a shear rate of 1000 sec$^{-1}$. The melt flow rate of the polylactic acid (on a dry basis) may also range from about 0.1 to about 40 grams per 10 minutes, in some embodiments from about 0.5 to about 20 grams per 10 minutes, and in some embodiments, from about 5 to about 15 grams per 10 minutes, determined at a load of 2160 grams and at 190° C.

Some types of neat polyesters (e.g., polylactic acid) can absorb water from the ambient environment such that it has a moisture content of about 500 to 600 parts per million ("ppm"), or even greater, based on the dry weight of the starting polylactic acid. Moisture content may be determined in a variety of ways as is known in the art, such as in accordance with ASTM D 7191-05, such as described below. Because the presence of water during melt processing can hydrolytically degrade the polyester and reduce its molecular weight, it is sometimes desired to dry the polyester prior to blending. In most embodiments, for example, it is desired that the polyester have a moisture content of about 300 parts per million ("ppm") or less, in some embodiments about 200 ppm or less, in some embodiments from about 1 to about 100 ppm prior to blending with the microinclusion and nanoinclusion additives. Drying of the polyester may occur, for instance, at a temperature of from about 50° C. to about 100° C., and in some embodiments, from about 70° C. to about 80° C.

B. Microinclusion Additive

As used herein, the term "microinclusion additive" generally refers to any amorphous, crystalline, or semi-crystalline material that is capable of being dispersed within the polymer matrix in the form of discrete domains of a microscale size. For example, prior to straining, the domains may have an average cross-sectional dimension of from about 0.05 μm to about 30 μm, in some embodiments from about 0.1 μm to about 25 μm, in some embodiments from about 0.5 μm to about 20 μm, and in some embodiments from about 1 μm to about 10 μm. The term "cross-sectional dimension" generally refers to a characteristic dimension (e.g., width or diameter) of a domain, which is substantially orthogonal to its major axis (e.g., length) and also typically substantially orthogonal to the direction of the stress applied during straining. While typically formed from the microinclusion additive, it should be also understood that the micro-scale domains may also be formed from a combination of the microinclusion and nanoinclusion additives and/or other components of the composition.

The microinclusion additive is generally polymeric in nature and possesses a relatively high molecular weight to help improve the melt strength and stability of the thermoplastic composition. Typically, the microinclusion polymer may be generally immiscible with the matrix polymer. In this manner, the additive can better become dispersed as discrete phase domains within a continuous phase of the matrix polymer. The discrete domains are capable of absorbing energy that arises from an external force, which increases the overall toughness and strength of the resulting material. The domains may have a variety of different shapes, such as elliptical, spherical, cylindrical, plate-like, tubular, etc. In one embodiment, for example, the domains have a substantially elliptical shape. The physical dimension of an individual domain is typically small enough to minimize the propagation of cracks through the polymeric material upon the application of an external stress, but large enough to initiate microscopic plastic deformation and allow for shear and/or stress intensity zones at and around particle inclusions.

While the polymers may be immiscible, the microinclusion additive may nevertheless be selected to have a solubility parameter that is relatively similar to that of the matrix polymer. This can improve the interfacial compatibility and physical interaction of the boundaries of the discrete and continuous phases, and thus reduces the likelihood that the composition will fracture. In this regard, the ratio of the solubility parameter for the matrix polymer to that of the additive is typically from about 0.5 to about 1.5, and in some embodiments, from about 0.8 to about 1.2. For example, the microinclusion additive may have a solubility parameter of from about 15 to about 30 MJoules$^{1/2}$/m$^{3/2}$, and in some embodiments, from about 18 to about 22 MJoules$^{1/2}$/m$^{3/2}$, while polylactic acid may have a solubility parameter of about 20.5 MJoules$^{1/2}$/m$^{3/2}$. The term "solubility parameter" as used herein refers to the "Hildebrand Solubility Parameter", which is the square root of the cohesive energy density and calculated according to the following equation:

$$\delta = \sqrt{((\Delta H_v - RT)/V_m)}$$

where:
ΔHv=heat of vaporization
R=ideal Gas constant
T=Temperature
Vm=Molecular Volume The Hildebrand solubility parameters for many polymers are also available from the Solubility Handbook of Plastics, by Wyeych (2004), which is incorporated herein by reference.

The microinclusion additive may also have a certain melt flow rate (or viscosity) to ensure that the discrete domains and resulting pores can be adequately maintained. For example, if the melt flow rate of the additive is too high, it tends to flow and disperse uncontrollably through the continuous phase. This results in lamellar, plate-like domains or co-continuous phase structures that are difficult to maintain and also likely to prematurely fracture. Conversely, if the melt flow rate of the additive is too low, it tends to clump together and form very large elliptical domains, which are difficult to disperse during blending. This may cause uneven distribution of the additive through the entirety of the continuous phase. In this regard, the present inventors have discovered that the ratio of the melt flow rate of the microinclusion additive to the melt flow rate of the matrix polymer is typically from about 0.2 to about 8, in some embodiments from about 0.5 to about 6, and in some embodiments, from about 1 to about 5. The microinclusion additive may, for example, have a melt flow rate of from about 0.1 to about 250 grams per 10 minutes, in some embodiments from about 0.5 to about 200 grams per 10 minutes, and in some embodiments, from about 5 to about 150 grams per 10 minutes, determined at a load of 2160 grams and at 190° C.

In addition to the properties noted above, the mechanical characteristics of the microinclusion additive may also be selected to achieve the desired porous network. For example, when a blend of the matrix polymer and microinclusion additive is applied with an external force, stress concentrations (e.g., including normal or shear stresses) and shear and/or plastic yielding zones may be initiated at and around the discrete phase domains as a result of stress concentrations that arise from a difference in the elastic modulus of the additive and matrix polymer. Larger stress concentrations promote more intensive localized plastic flow at the domains, which allows them to become significantly elongated when stresses are imparted. These elongated domains can allow the composition to exhibit a more pliable and softer behavior than the matrix polymer, such as when it is a rigid polyester resin. To enhance the stress concentrations, the microinclusion additive may be selected to have a relatively low Young's modulus of elasticity in comparison to the matrix polymer. For example, the ratio of the modulus of elasticity of the matrix polymer to that of the additive is typically from about 1 to about 250, in some embodiments from about 2 to about 100, and in some embodiments, from about 2 to about 50. The modulus of elasticity of the microinclusion additive may, for instance, range from about 2 to about 1000 Megapascals (MPa), in some embodiments from about 5 to about 500 MPa, and in some embodiments, from about 10 to about 200 MPa. To the contrary, the modulus of elasticity of polylactic acid, for example, is typically from about 800 MPa to about 3000 MPa.

While a wide variety of microinclusion additives may be employed that have the properties identified above, particularly suitable examples of such additives may include synthetic polymers, such as polyolefins (e.g., polyethylene, polypropylene, polybutylene, etc.); styrenic copolymers (e.g., styrene-butadiene-styrene, styrene-isoprene-styrene, styrene-ethylene-propylene-styrene, styrene-ethylene-butadiene-styrene, etc.); polytetrafluoroethylenes; polyesters (e.g., recycled polyester, polyethylene terephthalate, etc.); polyvinyl acetates (e.g., poly(ethylene vinyl acetate), polyvinyl chloride acetate, etc.); polyvinyl alcohols (e.g., polyvinyl alcohol, poly(ethylene vinyl alcohol), etc.); polyvinyl butyrals; acrylic resins (e.g., polyacrylate, polymethylacrylate, polymethylmethacrylate, etc.); polyamides (e.g., nylon); polyvinyl chlorides; polyvinylidene chlorides; polystyrenes; polyurethanes; etc. Suitable polyolefins may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, and so forth.

In one particular embodiment, the polymer is a propylene polymer, such as homopolypropylene or a copolymer of propylene. The propylene polymer may, for instance, be formed from a substantially isotactic polypropylene homopolymer or a copolymer containing equal to or less than about 10 wt. % of other monomer, i.e., at least about 90% by weight propylene. Such homopolymers may have a melting point of from about 160° C. to about 170° C.

In still another embodiment, the polyolefin may be a copolymer of ethylene or propylene with another α-olefin, such as a $C_3$-$C_{20}$ α-olefin or $C_3$-$C_{12}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Exemplary olefin copolymers for use in the present invention include ethylene-based copolymers available under the designation EXACT™ from ExxonMobil Chemical Company of Houston, Tex. Other suitable ethylene copolymers are available under the designation ENGAGE™, AFFINITY™, DOWLEX™ (LLDPE) and ATTANE™ (ULDPE) from Dow Chemical Company of Midland, Mich. Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al. Suitable propylene copolymers are also commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Suitable polypropylene homopolymers may likewise include Exxon Mobil 3155 polypropylene, Exxon Mobil Achieve™ resins, and Total M3661 PP resin. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al.

Any of a variety of known techniques may generally be employed to form the olefin copolymers. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al. and U.S. Pat. No. 6,090,325 to Wheat, et al. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

Regardless of the materials employed, the relative percentage of the microinclusion additive in the thermoplastic composition is selected to achieve the desired properties without significantly impacting the base properties of the composition. For example, the microinclusion additive is typically employed in an amount of from about 1 wt. % to about 30 wt. %, in some embodiments from about 2 wt. % to about 25 wt. %, and in some embodiments, from about 5 wt. % to about 20 wt. % of the thermoplastic composition, based on the weight of the continuous phase (matrix polymer(s)). The concentration of the microinclusion additive in the entire thermoplastic composition may likewise constitute from about 0.1 wt. % to about 30 wt. %, in some embodiments from about 0.5 wt. % to about 25 wt. %, and in some embodiments, from about 1 wt. % to about 20 wt. %.

C. Nanoinclusion Additive

As used herein, the term "nanoinclusion additive" generally refers to any amorphous, crystalline, or semi-crystalline material that is capable of being dispersed within the polymer matrix in the form of discrete domains of a nano-scale size. For example, prior to straining, the domains may have an average cross-sectional dimension of from about 1 to about 1000 nanometers, in some embodiments from about 5 to about 800 nanometers, in some embodiments from about 10 to about 500 nanometers, and in some embodiments from about 20 to about 200 nanometers. It should be also understood that the nano-scale domains may also be formed from a combination of the microinclusion and nanoinclusion additives and/or other components of the composition. The nanoinclusion additive is typically employed in an amount of from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase (matrix polymer(s)). The concentration of the nanoinclusion additive in the entire thermoplastic composition may likewise be from about 0.01 wt. % to about 15 wt. %, in some embodiments from about 0.05 wt. % to about 10 wt. %, and in some embodiments, from about 0.3 wt. % to about 6 wt. % of the thermoplastic composition.

The nanoinclusion additive may be polymeric in nature and possess a relatively high molecular weight to help improve the melt strength and stability of the thermoplastic composition. To enhance its ability to become dispersed into nano-scale domains, the nanoinclusion additive may also be selected from materials that are generally compatible with the matrix polymer and the microinclusion additive. This may be particularly useful when the matrix polymer or the microinclusion additive possesses a polar moiety, such as a polyester. One example such a nanoinclusion additive is a functionalized polyolefin. The polar component may, for example, be provided by one or more functional groups and the non-polar component may be provided by an olefin. The olefin component of the nanoinclusion additive may generally be formed from any linear or branched α-olefin monomer, oligomer, or polymer (including copolymers) derived from an olefin monomer, such as described above.

The functional group of the nanoinclusion additive may be any group, molecular segment and/or block that provides a polar component to the molecule and is not compatible with the matrix polymer. Examples of molecular segment and/or blocks not compatible with polyolefin may include acrylates, styrenics, polyesters, polyamides, etc. The functional group can have an ionic nature and comprise charged metal ions. Particularly suitable functional groups are maleic anhydride, maleic acid, fumaric acid, maleimide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond®, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation Polybond® and Eastman Chemical Company under the designation Eastman G series.

In certain embodiments, the nanoinclusion additive may also be reactive. One example of such a reactive nanoinclusion additive is a polyepoxide that contains, on average, at least two oxirane rings per molecule. Without intending to be limited by theory, it is believed that such polyepoxide molecules can induce reaction of the matrix polymer (e.g., polyester) under certain conditions, thereby improving its melt strength without significantly reducing glass transition temperature. The reaction may involve chain extension, side chain branching, grafting, copolymer formation, etc. Chain extension, for instance, may occur through a variety of different reaction pathways. For instance, the modifier may enable a nucleophilic ring-opening reaction via a carboxyl terminal group of a polyester (esterification) or via a hydroxyl group (etherification). Oxazoline side reactions may likewise occur to form esteramide moieties. Through such reactions, the molecular weight of the matrix polymer may be increased to counteract the degradation often observed during melt processing. While it may be desirable to induce a reaction with the matrix polymer as described above, the present inventors have discovered that too much of a reaction can lead to crosslinking between polymer backbones. If such crosslinking is allowed to proceed to a significant extent, the resulting polymer blend can become brittle and difficult to process into a material with the desired strength and elongation properties.

In this regard, the present inventors have discovered that polyepoxides having a relatively low epoxy functionality are particularly effective, which may be quantified by its "epoxy equivalent weight." The epoxy equivalent weight reflects the amount of resin that contains one molecule of an epoxy group, and it may be calculated by dividing the number average molecular weight of the modifier by the number of epoxy groups in the molecule. The polyepoxide of the present invention typically has a number average molecular weight from about 7,500 to about 250,000 grams per mole, in some embodiments from about 15,000 to about 150,000 grams per mole, and in some embodiments, from about 20,000 to 100,000 grams per mole, with a polydispersity index typically ranging from 2.5 to 7. The polyepoxide may contain less than 50, in some embodiments from 5 to 45, and in some embodiments, from 15 to 40 epoxy groups. In turn, the epoxy equivalent weight may be less than about 15,000 grams per mole, in some embodiments from about 200 to about 10,000 grams per mole, and in some embodiments, from about 500 to about 7,000 grams per mole.

The polyepoxide may be a linear or branched, homopolymer or copolymer (e.g., random, graft, block, etc.) containing terminal epoxy groups, skeletal oxirane units, and/or pendent epoxy groups. The monomers employed to form such polyepoxides may vary. In one particular embodiment, for example, the polyepoxide contains at least one epoxy-functional (meth)acrylic monomeric component. As used herein, the term "(meth)acrylic" includes acrylic and methacrylic monomers, as well as salts or esters thereof, such as acrylate and methacrylate monomers. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate.

The polyepoxide typically has a relatively high molecular weight, as indicated above, so that it may not only result in chain extension, but also help to achieve the desired blend morphology. The resulting melt flow rate of the polymer is thus typically within a range of from about 10 to about 200 grams per 10 minutes, in some embodiments from about 40 to about 150 grams per 10 minutes, and in some embodiments, from about 60 to about 120 grams per 10 minutes, determined at a load of 2160 grams and at a temperature of 190° C.

If desired, additional monomers may also be employed in the polyepoxide to help achieve the desired molecular weight. Such monomers may vary and include, for example, ester monomers, (meth)acrylic monomers, olefin monomers, amide monomers, etc. In one particular embodiment, for example, the polyepoxide includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene.

Another suitable monomer may include a (meth)acrylic monomer that is not epoxy-functional. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof.

In one particularly desirable embodiment of the present invention, the polyepoxide is a terpolymer formed from an epoxy-functional (meth)acrylic monomeric component, α-olefin monomeric component, and non-epoxy functional (meth)acrylic monomeric component. For example, the polyepoxide may be poly(ethylene-co-methylacrylate-co-glycidyl methacrylate), which has the following structure:

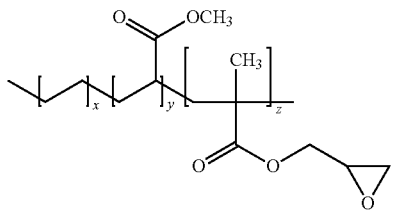

wherein, x, y, and z are 1 or greater.

The epoxy functional monomer may be formed into a polymer using a variety of known techniques. For example, a monomer containing polar functional groups may be grafted onto a polymer backbone to form a graft copolymer. Such grafting techniques are well known in the art and described, for instance, in U.S. Pat. No. 5,179,164. In other embodiments, a monomer containing epoxy functional groups may be copolymerized with a monomer to form a block or random copolymer using known free radical polymerization techniques, such as high pressure reactions, Ziegler-Natta catalyst reaction systems, single site catalyst (e.g., metallocene) reaction systems, etc.

The relative portion of the monomeric component(s) may be selected to achieve a balance between epoxy-reactivity and melt flow rate. More particularly, high epoxy monomer contents can result in good reactivity with the matrix polymer, but too high of a content may reduce the melt flow rate to such an extent that the polyepoxide adversely impacts the melt strength of the polymer blend. Thus, in most embodiments, the epoxy-functional (meth)acrylic monomer(s) constitute from about 1 wt. % to about 25 wt. %, in some embodiments from about 2 wt. % to about 20 wt. %, and in some embodiments, from about 4 wt. % to about 15 wt. % of the copolymer. The α-olefin monomer(s) may likewise constitute from about 55 wt. % to about 95 wt. %, in some embodiments from about 60 wt. % to about 90 wt. %, and in some embodiments, from about 65 wt. % to about 85 wt. % of the copolymer. When employed, other monomeric components (e.g., non-epoxy functional (meth)acrylic monomers) may constitute from about 5 wt. % to about 35 wt. %, in some embodiments from about 8 wt. % to about 30 wt. %, and in some embodiments, from about 10 wt. % to about 25 wt. % of the copolymer. One specific example of a suitable polyepoxide that may be used in the present invention is commercially available from Arkema under the name LOTADER® AX8950 or AX8900. LOTADER® AX8950, for instance, has a melt flow rate of 70 to 100 g/10 min and has a glycidyl methacrylate monomer content of 7 wt. % to 11 wt. %, a methyl acrylate monomer content of 13 wt. % to 17 wt. %, and an ethylene monomer content of 72 wt. % to 80 wt. %. Another suitable polyepoxide is commercially available from DuPont under the name ELVALOY® PTW, which is a terpolymer of ethylene, butyl acrylate, and glycidyl methacrylate and has a melt flow rate of 12 g/10 min.

In addition to controlling the type and relative content of the monomers used to form the polyepoxide, the overall weight percentage may also be controlled to achieve the desired benefits. For example, if the modification level is too low, the desired increase in melt strength and mechanical properties may not be achieved. The present inventors have also discovered, however, that if the modification level is too high, processing may be restricted due to strong molecular interactions (e.g., crosslinking) and physical network formation by the epoxy functional groups. Thus, the polyepoxide is typically employed in an amount of from about 0.05 wt. % to about 10 wt. %, in some embodiments from about 0.1 wt % to about 8 wt. %, in some embodiments from about 0.5 wt. % to about 5 wt. %, and in some embodiments, from about 1 wt. % to about 3 wt. %, based on the weight of the matrix polymer employed in the composition. The polyepoxide may also constitute from about 0.05 wt. % to about 10 wt. %, in some embodiments from about 0.05 wt. % to about 8 wt. %, in some embodiments from about 0.1 wt. % to about 5 wt. %, and in some embodiments, from about 0.5 wt. % to about 3 wt. %, based on the total weight of the composition.

Other reactive nanoinclusion additives may also be employed in the present invention, such as oxazoline-functionalized polymers, cyanide-functionalized polymers, etc. When employed, such reactive nanoinclusion additives may be employed within the concentrations noted above for the polyepoxide. In one particular embodiment, an oxazoline-grafted polyolefin may be employed that is a polyolefin grafted with an oxazoline ring-containing monomer. The oxazoline may include a 2-oxazoline, such as 2-vinyl-2-oxazoline (e.g., 2-isopropenyl-2-oxazoline), 2-fatty-alkyl-2-oxazoline (e.g., obtainable from the ethanolamide of oleic acid, linoleic acid, palmitoleic acid, gadoleic acid, erucic acid and/or arachidonic acid) and combinations thereof. In another embodiment, the oxazoline may be selected from ricinoloxazoline maleinate, undecyl-2-oxazoline, soya-2- oxazoline, ricinus-2-oxazoline and combinations thereof, for example. In yet another embodiment, the oxazoline is selected from 2-isopropenyl-2-oxazoline, 2-isopropenyl-4,4-dimethyl-2-oxazoline and combinations thereof.

Nanofillers may also be employed, such as carbon black, carbon nanotubes, carbon nanofibers, nanoclays, metal nanoparticles, nanosilica, nanoalumina, etc. Nanoclays are particularly suitable. The term "nanoclay" generally refers to nanoparticles of a clay material (a naturally occurring mineral, an organically modified mineral, or a synthetic nanomaterial), which typically have a platelet structure. Examples of nanoclays include, for instance, montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc. An example of a suitable nanoclay is Cloisite®, which is a montmorillonite nanoclay and commercially available from Southern Clay Products, Inc. Other examples of synthetic nanoclays include but are not limited to a mixed-metal hydroxide nanoclay, layered double hydroxide nanoclay (e.g., sepiocite), laponite, hectorite, saponite, indonite, etc.

If desired, the nanoclay may contain a surface treatment to help improve compatibility with the matrix polymer (e.g., polyester). The surface treatment may be organic or inorganic. In one embodiment, an organic surface treatment is employed that is obtained by reacting an organic cation with the clay. Suitable organic cations may include, for instance, organoquaternary ammonium compounds that are capable of exchanging cations with the clay, such as dimethyl bis[hydrogenated tallow] ammonium chloride (2M2HT), methyl benzyl bis[hydrogenated tallow] ammonium chloride (MB2HT), methyl tris[hydrogenated tallow alkyl] chloride (M3HT), etc. Examples of commercially available organic nanoclays may include, for instance, Dellite® 43B (Laviosa Chimica of Livorno, Italy), which is a montmorillonite clay modified with dimethyl benzylhydrogenated tallow ammonium salt. Other examples include Cloisite® 25A and Cloisite® 30B (Southern Clay Products) and Nanofil 919 (Süd Chemie). If desired, the nanofiller can be blended with a carrier resin to form a masterbatch that enhances the compatibility of the additive with the other polymers in the composition. Particularly suitable carrier resins include, for instance, polyesters (e.g., polylactic acid, polyethylene terephthalate, etc.); polyolefins (e.g., ethylene polymers, propylene polymers, etc.); and so forth, as described in more detail above.

In certain embodiments of the present invention, multiple nanoinclusion additives may be employed in combination. For instance, a first nanoinclusion additive (e.g., polyepoxide) may be dispersed in the form of domains having an average cross-sectional dimension of from about 50 to about 500 nanometers, in some embodiments from about 60 to about 400 nanometers, and in some embodiments from about 80 to about 300 nanometers. A second nanoinclusion additive (e.g., nanofiller) may also be dispersed in the form of domains that are smaller than the first nanoinclusive additive, such as those having an average cross-sectional dimension of from about 1 to about 50 nanometers, in some embodiments from about 2 to about 45 nanometers, and in some embodiments from about 5 to about 40 nanometers. When employed, the first and/or second nanoinclusion additives typically constitute from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase (matrix polymer(s)). The concentration of the first and/or second nanoinclusion additives in the entire thermoplastic composition may likewise be from about 0.01 wt. % to about 15 wt. %, in some embodiments from about 0.05 wt. % to about 10 wt. %, and in some embodiments, from about 0.1 wt. % to about 8 wt. % of the thermoplastic composition.

D. Other Components

A wide variety of ingredients may be employed in the composition for a variety of different reasons. For instance, in one particular embodiment, an interphase modifier may be employed in the thermoplastic composition to help reduce the degree of friction and connectivity between the microinclusion additive and matrix polymer, and thus enhance the degree and uniformity of debonding. In this manner, the pores can become distributed in a more homogeneous fashion throughout the composition. The modifier may be in a liquid or semi-solid form at room temperature (e.g., 25° C.) so that it possesses a relatively low viscosity, allowing it to be more readily incorporated into the thermoplastic composition and to easily migrate to the polymer surfaces. In this regard, the kinematic viscosity of the interphase modifier is typically from about 0.7 to about 200 centistokes ("cs"), in some embodiments from about 1 to about 100 cs, and in some embodiments, from about 1.5 to about 80 cs, determined at 40° C. In addition, the interphase modifier is also typically hydrophobic so that it has an affinity for the microinclusion additive, for example, resulting in a change in the interfacial tension between the matrix polymer and the additive. By reducing physical forces at the interfaces between the matrix polymer and the microinclusion additive, it is believed that the low viscosity, hydrophobic nature of the modifier can help facilitate debonding. As used herein, the term "hydrophobic" typically refers to a material having a contact angle of water in air of about 40° or more, and in some cases, about 60° or more. In contrast, the term "hydrophilic" typically refers to a material having a contact angle of water in air of less than about 40°. One suitable test for measuring the contact angle is ASTM D5725-99 (2008).

Suitable hydrophobic, low viscosity interphase modifiers may include, for instance, silicones, silicone-polyether copolymers, aliphatic polyesters, aromatic polyesters, alkylene glycols (e.g., ethylene glycol, diethylene glycol, triethylene glycol, tetraethylene glycol, propylene glycol, polyethylene glycol, polypropylene glycol, polybutylene glycol, etc.), alkane diols (e.g., 1,3-propanediol, 2,2-dimethyl-1,3-propanediol, 1,3-butanediol, 1,4-butanediol, 1,5-pentanediol, 1,6-hexanediol, 2,2,4-trimethyl-1,6 hexanediol, 1,3-cyclohexanedimethanol, 1,4-cyclohexanedimethanol, 2,2,4,4-tetramethyl-1,3-cyclobutanediol, etc.), amine oxides (e.g., octyldimethylamine oxide), fatty acid esters, fatty acid amides (e.g., oleamide, erucamide, stearamide, ethylene bis(stearamide), etc.), mineral, and vegetable oils, and so forth. One particularly suitable liquid or semi-solid is polyether polyol, such as commercially available under the trade name Pluriol® WI from BASF Corp. Another suitable modifier is a partially renewable ester, such as commercially available under the trade name HALLGREEN® IM from Hallstar.

When employed, the interphase modifier may constitute from about 0.1 wt. % to about 20 wt. %, in some embodiments from about 0.5 wt. % to about 15 wt. %; and in some embodiments, from about 1 wt. % to about 10 wt. % of the thermoplastic composition, based on the weight of the continuous phase (matrix polymer(s)). The concentration of the interphase modifier in the entire thermoplastic composition may likewise constitute from about 0.05 wt. % to about 20 wt. %, in some embodiments from about 0.1 wt. % to about 15 wt. %, and in some embodiments, from about 0.5 wt. % to about 10 wt. %.

When employed in the amounts noted above, the interphase modifier has a character that enables it to readily migrate to the interfacial surface of the polymers and facilitate debonding without disrupting the overall melt properties of the thermoplastic composition. For example, the interphase modifier does not typically have a plasticizing effect on the polymer by reducing its glass transition temperature. Quite to the contrary, the present inventors have discovered that the glass transition temperature of the thermoplastic composition may be substantially the same as the initial matrix polymer. In this regard, the ratio of the glass temperature of the composition to that of the matrix polymer is typically from about 0.7 to about 1.3, in some embodiments from about 0.8 to about 1.2, and in some embodiments, from about 0.9 to about 1.1. The thermoplastic composition may, for example, have a glass transition temperature of from about 35° C. to about 80° C., in some embodiments from about 40° C. to about 80° C., and in some embodiments, from about 50° C. to about 65° C. The melt flow rate of the thermoplastic composition may also be similar to that of the matrix polymer. For example, the melt flow rate of the composition (on a dry basis) may be from about 0.1 to about 70 grams per 10 minutes, in some embodiments from about 0.5 to about 50 grams per 10 minutes, and in some embodiments, from about 5 to about 25 grams per 10 minutes, determined at a load of 2160 grams and at a temperature of 190° C.

Compatibilizers may also be employed that improve interfacial adhesion and reduce the interfacial tension between the domain and the matrix, thus allowing the formation of smaller domains during mixing. Examples of suitable compatibilizers may include, for instance, copolymers functionalized with epoxy or maleic anhydride chemical moieties. An example of a maleic anhydride compatibilizer is polypropylene-grafted-maleic anhydride, which is commercially available from Arkema under the trade names Orevac™ 18750 and Orevac™ CA 100. When employed, compatibilizers may constitute from about 0.05 wt. % to about 10 wt. %, in some embodiments from about 0.1 wt. % to about 8 wt. %, and in some embodiments, from about 0.5 wt. % to about 5 wt. % of the thermoplastic composition, based on the weight of the continuous phase matrix.

Other suitable materials that may also be used in the thermoplastic composition, such as catalysts, antioxidants, stabilizers, surfactants, waxes, solid solvents, fillers, nucleating agents (e.g., calcium carbonate, etc.), plasticizers, particulates, and other materials added to enhance the processability and mechanical properties of the thermoplastic composition.

To form the thermoplastic composition, the components are typically blended together using any of a variety of known techniques. In one embodiment, for example, the components may be supplied separately or in combination. For instance, the components may first be dry mixed together to form an essentially homogeneous dry mixture, and they may likewise be supplied either simultaneously or in sequence to a melt processing device that dispersively blends the materials. Batch and/or continuous melt processing techniques may be employed. For example, a mixer/kneader, Banbury mixer, Farrel continuous mixer, single-screw extruder, twin-screw extruder, roll mill, etc., may be utilized to blend and melt process the materials. Particularly suitable melt processing devices may be a co-rotating, twin-screw extruder (e.g., ZSK-30 extruder available from Werner & Pfleiderer Corporation of Ramsey, N.J. or a Thermo Prism™ USALAB 16 extruder available from Thermo Electron Corp., Stone, England). Such extruders may include feeding and venting ports and provide high intensity distributive and dispersive mixing. For example, the components may be fed to the same or different feeding ports of the twin-screw extruder and melt blended to form a substantially homogeneous melted mixture. If desired, other additives may also be injected into the polymer melt and/or separately fed into the extruder at a different point along its length.

Regardless of the particular processing technique chosen, the resulting melt blended composition typically contains micro-scale domains of the microinclusion additive and nano-scale domains of the nanoinclusion additive as described above. The degree of shear/pressure and heat may be controlled to ensure sufficient dispersion, but not so high as to adversely reduce the size of the domains so that they are incapable of achieving the desired properties. For example, blending typically occurs at a temperature of from about 180° C. to about 300° C., in some embodiments from about 185° C. to about 250° C., and in some embodiments, from about 190° C. to about 240° C. Likewise, the apparent shear rate during melt processing may range from about 10 seconds$^{-1}$ to about 3000 seconds$^{-1}$, in some embodiments from about 50 seconds$^{-1}$ to about 2000 seconds$^{-1}$, and in some embodiments, from about 100 seconds$^{-1}$ to about 1200 seconds$^{-1}$. The apparent shear rate may be equal to $4Q/\pi R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, may also be controlled to achieve the desired degree of homogeneity.

To achieve the desired shear conditions (e.g., rate, residence time, shear rate, melt processing temperature, etc.), the speed of the extruder screw(s) may be selected with a certain range. Generally, an increase in product temperature is observed with increasing screw speed due to the additional mechanical energy input into the system. For example, the screw speed may range from about 50 to about 600 revolutions per minute ("rpm"), in some embodiments from about 70 to about 500 rpm, and in some embodiments, from about 100 to about 300 rpm. This may result in a temperature that is sufficient high to disperse the microinclusion additive without adversely impacting the size of the resulting domains. The melt shear rate, and in turn the degree to which the additives are dispersed, may also be increased through the use of one or more distributive and/or dispersive mixing elements within the mixing section of the extruder. Suitable distributive mixers for single screw extruders may include, for instance, Saxon, Dulmage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin (VIP) mixers.

II. Polymeric Material

The thermoplastic composition may be formed into a polymeric material having any of a variety of different forms depending on the particular application, such as films, fibrous materials, particles etc., as well as composites and laminates thereof. In one embodiment, for example, the polymeric material is in the form of a film or layer of a film. Multilayer films may contain from two (2) to fifteen (15) layers, and in some embodiments, from three (3) to twelve (12) layers. Such multilayer films normally contain at least one base layer and at least one additional layer (e.g., skin layer), but may contain any number of layers desired. For example, the multilayer film may be formed from a base layer and one or more skin layers, wherein the base layer and/or skin layer(s) are formed from the polymeric material of the present invention. It should be understood, however, that other polymer materials may also be employed in the base layer and/or skin layer(s), such as polyolefin polymers.

Fibers may also be formed from the thermoplastic composition in accordance with the present invention. The fibers may be discontinuous fibers having a definite length (e.g., staple fibers) or substantially continuous filaments. The fibers may generally have any desired configuration, including monocomponent and multicomponent (e.g., sheath-core configuration, side-by-side configuration, segmented pie configuration, island-in-the-sea configuration, and so forth). In some embodiments, the fibers may contain one or more additional polymers as a component (e.g., bicomponent) or constituent (e.g., biconstituent) to further enhance strength, processability, and/or other properties. For instance, the thermoplastic composition may form a sheath component of a sheath/core bicomponent fiber, while an additional polymer may form the core component, or vice versa. The additional polymer may be any polymer desired, such as polyesters, e.g., polylactic acid, polyethylene terephthalate, etc.; polyolefins, e.g., polyethylene, polypropylene, polybutylene, and so forth; polytetrafluoroethylene; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; and polyurethanes.

If desired, the fibers may also be incorporated into a fibrous material, such as a woven fabric, knit fabric, nonwoven web, etc. For example, the fibers may be formed into a nonwoven web structure by randomly depositing the fibers onto a forming surface (optionally with the aid of a vacuum) and then bonding the resulting web using any known technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with the polymer used to form the fibers. Suitable autogenous bonding techniques may include ultrasonic bonding, thermal bonding, through-air bonding, calendar bonding, and so forth. For example, the web may be further bonded or embossed with a pattern by a thermo-mechanical process in which the web is passed between a heated smooth anvil roll and a heated pattern roll. The pattern roll may have any raised pattern which provides the desired web properties or appearance. Desirably, the pattern roll defines a raised pattern which defines a plurality of bond locations which define a bond area between about 2% and 30% of the total area of the roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et. al., as well as U.S. Design Pat. Nos. 428,267 to Romano et al.; 390,708 to Brown; 418,305 to Zander, et al.; 384,508 to Zander, et al.; 384,819 to Zander, et al.; 358,035 to Zander, et al.; and 315,990 to Blenke, et al. As is well known to those skilled in the art, the temperature and pressure required may vary depending upon many factors including but not limited to, pattern bond area, polymer properties, fiber properties and nonwoven properties.

A variety of nonwoven webs may be formed from the thermoplastic composition in accordance with the present invention, such as spunbond webs, meltblown webs, bonded carded webs, wet-laid webs, airlaid webs, coform webs, hydraulically entangled webs, etc. If desired, the nonwoven web may also be a composite that contains a combination of fibers formed according to the present invention and other types of fibers (e.g., staple fibers, filaments, etc.). For example, additional synthetic fibers may be utilized, such as those formed from polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; etc. If desired, renewable polymers may also be employed. Some examples of known synthetic fibers include sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del. Polylactic acid staple fibers may also be employed, such as those commercially available from Far Eastern Textile, Ltd. of Taiwan.

The composite may also contain pulp fibers, such as high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), bamboo, combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Washington under the trade designation of "NF-405." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, *eucalyptus*, maple, birch, aspen, etc. *Eucalyptus* kraft pulp fibers may be particularly desired to increase softness, enhance brightness, increase opacity, and change the pore structure of the sheet to increase its wicking ability. Bamboo or cotton fibers may also be employed.

Nonwoven composites may be formed using a variety of known techniques. For example, the nonwoven composite may be a "coform material" that contains a mixture or stabilized matrix of fibers formed according to the present invention and an absorbent material. As an example, coform materials may be made by a process in which at least one meltblown die head is arranged near a chute through which the absorbent materials are added to the web while it is forming. Such absorbent materials may include, but are not limited to, pulp fibers, superabsorbent particles, inorganic and/or organic absorbent materials, treated polymeric staple fibers, and so forth. The relative percentages of the absorbent material may vary over a wide range depending on the desired characteristics of the nonwoven composite. For example, the nonwoven composite may contain from about 1 wt. % to about 60 wt. %, in some embodiments from 5 wt. % to about 50 wt. %, and in some embodiments, from about 10 wt. % to about 40 wt. % thermoplastic composition fibers. The nonwoven composite may likewise contain from about 40 wt. % to about 99 wt. %, in some embodiments from 50 wt. % to about 95 wt. %, and in some embodiments, from about 60 wt. % to about 90 wt. %/o absorbent material. Some examples of such coform materials are disclosed in U.S. Pat. No. 4,100,324 to Anderson, et al.; U.S. Pat. No. 5,284,703 to Everhart, et al; and U.S. Pat. No. 5,350,624 to Georger, et al.

Nonwoven laminates may also be formed in the present invention in which one or more layers are formed from fibers of the present invention. For example, the nonwoven web of one layer may be a spunbond web that contains fibers of the present invention, while the nonwoven web of another layer contains fibers of the present invention and/or other types of fibers. In one embodiment, the nonwoven laminate contains a meltblown layer positioned between two spunbond layers to form a spunbond/meltblown/spunbond ("SMS") laminate. If desired, the spunbond layer(s) may be formed from the fibers of the present invention. Various techniques for forming SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., as well as U.S. Patent Application Publication No. 2004/0002273 to Fitting, et al. Of course, the nonwoven laminate may have other configuration and possess any desired number of meltblown and spunbond layers, such as spunbond/meltblown/meltblown/spunbond laminates ("SMMS"), spunbond/meltblown laminates ("SM"), etc. Although the basis weight of the nonwoven laminate may be tailored to the desired application, it generally ranges from about 10 to about 300 grams per square meter ("gsm"), in some embodiments from about 25 to about 200 gsm, and in some embodiments, from about 40 to about 150 gsm.

Of course, in addition to films, fibers, or fibrous materials, the polymeric material may also possess other forms as is known in the art. For example, the polymeric material may be in the form of particles. The particles may possess any desired shape, such as flake, nodular, spherical, tube, etc., and may include the thermoplastic composition described above, as well as other materials, coatings, etc. The size of the particles may be controlled to optimize the release of the active agent for a particular application. For example, the particles may have a median size (e.g., diameter) of from about 1 to about 2,000 micrometers, in some embodiments from about 10 to about 1,000 micrometers, and in some embodiments, from about 100 to about 600 micrometers. The term "median" particle size as used herein refers to the "D50" particle size distribution of the particles, which means that at least 50% of the particles have the size indicated. The particles may likewise have a D90 particle size distribution (at least 90% of the particles have the size indicated) within the ranges noted above.

When employed, particles may be formed using any of a variety of conventional techniques. In certain embodiments, various forms of the thermoplastic composition (e.g., pellets, sheets, films, fibers, bars, etc.) may simply be downsized into the desired particles through a mechanical process. For instance, impact downsizing, which typically employs a grinder having a rotating grinding element, may be used to form the desired particles. Repeated impact and/or shear stress can be created between the rotating grinding element and a stationary or counter-rotating grinding element. Impact downsizing may also employ air flow to carry and collide the material into a grinding disk (or other shearing element). One particularly suitable impact downsizing apparatus is available commercially from Pallmann Industries (Clifton, N.J.) under the name Turbofiner®, type PLM. In this apparatus, a high activity air whirl is created within a cylindrical grinding chamber between a stationary grinding element and a rotating grinding element of an impact grinding mill. Due to the high air volume, pellets can be impacted against each other and become downsized into the desired particle size. Other suitable impact downsizing processes may be described in U.S. Pat. Nos. 6,431,477 and 7,510,133, both to Pallmann.

Another suitable particle formation process is cold extrusion downsizing, which generally employs shear and compression forces to form the particles. For example, the material can be forced through a die at temperatures below the melting point of the matrix polymer. Solid-state shear pulverization is another suitable process that can be used. Such processes generally involve continuous extrusion of the material under high shear and compression conditions while the extruder barrels and a screw are cooled to prevent polymer melting. Examples of such solid state pulverization techniques are described, for instance, in U.S. Pat. No. 5,814,673 to Khait; U.S. Pat. No. 6,479,003 to Furgiuele, et al.; U.S. Pat. No. 6,494,390 to Khait. et al.; U.S. Pat. No. 6,818,173 to Khait; and U.S. Publ. No. 2006/0178465 to Torkelson, et al. Yet another particle formation technique is known as cryogenic disk milling. Cryogenic disk milling generally employs a liquid (e.g., liquid nitrogen) to cool or freeze the material prior to and/or during grinding. In one embodiment, a single-runner disk milling apparatus can be employed that has a stationary disk and a rotating disk. Material enters between the discs via a channel near the disk center and is formed into particles through the frictional forces created between the discs. One suitable cryogenic disk milling apparatus is available under the name Wedco® cryogenic grinding system from ICO Polymers (Allentown, Pa.).

III. Active Agents

As used herein, the term "active agent" generally refers to any compound or mixture of compounds that can produce a certain result. The active agent may be provided in a variety of different forms (e.g., liquid, solid, gel, slurry, nano-metal particles, nanoclay, etc.) and may be selected from a variety of known classes of compounds. Active agents may include biologically active agents, chemically active agents, as well as combinations thereof. Biologically active agents, for instance, typically achieve the desired result (e.g., physiological) upon contact with a living organism (e.g., a mammal, such as a human) and/or a surface with which a living organism may come into contact. Some examples of suitable biologically active agents may include, for instance, proteins, peptides, nucleotides, anti-obesity drugs, nutraceuticals, dietary supplements, carotenoids, corticosteroids, elastase inhibitors, antimicrobially active compounds (e.g., biocides, antifungal agents, antibiotics, antibacterial agents, etc.), anti-allergic agents, anti-emetics, analgesics, cardiovascular agents, anti-inflammatory agents, anthelmintics, anti-arrhythmic agents, anticoagulants, antidepressants, antidiabetic agents, antiepileptics, antihistamines, antihypertensive agents, antimuscarinic agents, antineoplastic agents, antioxidants (e.g., Vitamin E), immunosuppressants, anti-thyroid agents, anxiolytic sedatives (hypnotics and neuroleptics), astringents, beta-adrenoceptor blocking agents, blood products and substitutes, cardiac inotropic agents, contrast media, corticosteroids, cosmetics, cough suppressants (expectorants and mucolytics), deodorants, dermal agents (e.g., acne medication, anti-wrinkle drugs, etc.), diagnostic agents, diagnostic imaging agents, diuretics, dopaminergics (antiparkinsonian agents), emollients, fragrances, haemostatics, immunological agents, insect repellants, lipid regulating agents, moisturizers, muscle relaxants, oncology therapies, parasympathomimetics, parathyroid calcitonin and biphosphonates, prostaglandins, radio-pharmaceuticals, sex hormones (including steroids), sunscreens, stimulants and anoretics (e.g., caffeine), sympathomimetics, thyroid agents, vasodilators, and xanthines.

Particularly suitable biologically active agents for use in the present invention are those agents that can be topically applied to a surface (e.g., human body, hard surface, etc.), such as antimicrobial actives, sunscreens, cosmetics, dermal agents, fragrances, insect repellants, moisturizers, deodorants, etc. In one particular embodiment, for example, the active agent may be an antimicrobial active. One class of antimicrobial actives that may be employed in the present invention are botanical oils. The botanical oil may be an "essential" oil that is extracted from a plant. Likewise, the botanical oil may also be isolated or purified from an essential oil, or it may simply be made synthetically to mimic a compound derived from a plant (e.g., synthetically made thymol). The botanical oils are generally soluble in lipids and believed to exhibit antimicrobial efficacy due to their ability to cause damage to the lipid component of the cell membrane in microorganisms, thereby inhibiting their proliferation. Essential oils are derived from herbs, flowers, trees, and other plants, and are typically present as tiny droplets between the cells of the plants and may be extracted by methods known to those of skill in the art (e.g., steam distillation, enfleurage (i.e., extraction using fat(s)), maceration, solvent extraction, or mechanical pressing). Examples of suitable essential oils for use in the present invention may include, for instance, anise oil, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, *eucalyptus* oil, vervain oil, peppermint oil, gum benzoin, basil oil, fennel oil, fir oil, balsam oil, menthol, ocmea *origanum* oil, Hydastis carradensis oil, Berberidaceae daceae oil, Ratanhiae and *Curcuma longa* oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, or vetiver oil. Still other essential oils known to those of skill in the art are also contemplated as being useful within the context of the present invention (e.g., International Cosmetic Ingredient Dictionary, $10^{th}$ and $12^{th}$ editions, 2004 and 2008, respectively).

Carvacrol and thymol-containing oils may be purified from the species *Origanum vulgare* of a *hirtum* variety. Ideally this is a hybrid strain that produces high quality oils, but is not limited to this genus, species or strain. The oil extract may also be obtained from a plant of the genus *Nepeta* including, but not limited to species *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinil, Nepeta nepetela, Nepeta sibthorpii, Nepeta subsessilis, Nepeta tuberosa, Thymus glandulosus, Thymus hyemalis, Thymus vulgaris* and *Thymus zygis*.

As indicated above, isolates and/or derivatives of essential oils may also be employed. For example, monoterpene phenols are particularly suitable, which may be isolated and purified from plant oil extracts, or made synthetically by known methods. Suitable monoterpene phenols may include, for instance, thymol, carvacrol, eucalyptol, etc. Thymol (isopropyl-cresol) is one particularly suitable monoterpene phenol, which is a crystalline substance that has a boiling point of about 238° C. at atmospheric pressure. Carvacrol (isopropyl-o-cresol), an isomer of thymol, is another suitable compound. Carvacrol is a liquid with a boiling point of about 233° C. at atmospheric pressure. Thymol and carvacrol, as well as isomers thereof, may be derived from plant oil extracts or synthesized. For example, carvacrol may be synthesized by the reaction of nitrous acid with 1-methyl-2-amino-4-propyl benzene. In addition to being employed in an isolated or pre-synthesized form, essential oils containing the monoterpene phenols as major constituents may be employed, with the final concentrations of the monoterpene phenols being within the ranges provided herein. The term "major constituent" generally refers to those essential oils having monoterpene phenols in an amount of more than 50 wt. %. It is well-known in the art that such essential oils may also contain lesser amounts of other constituents, such as non-aromatic terpene compounds. Essential oils with organic phenolic compounds as the major constituent include, for example, anise oil, bay oil terpineless, clove bud, clove leaf, clove oil, clove stem, *origanum* oil, Peru balsam, pimento oil, *eucalyptus* oil, and thyme oil.

In addition to botanical oils, other known antimicrobial actives may also be employed in the present invention. Some examples of such actives may include, for instance, metal particles (e.g., nano-metals), nanoclays, halogenated compounds (e.g., p-chlorometaxylenol ("PCMX"), 2,4,4'-trichloro-2 hydroxy di-phenyl ether ("triclosan"), chlorhexidine gluconate ("CHG"), etc.); biguanide compounds (e.g., polyhexamethylene biguanide ("PHMB")); quaternary ammonium compounds (e.g., behenalkonium chloride, cetyl pyridinium chloride, organosilicone-based quaternary ammonium compounds, etc.), and so forth.

As noted above, chemically active agents may also be employed in the present invention. Without limitation, some examples of such agents may include, for instance, antioxidants, such as vitamin E, tocopheryl acetate, retinyl palmitate, magnesium ascorbyl phosphate, etc.; viscosity modifiers; lubricants; fire or flame retardants; fertilizer compounds; and so forth.

Regardless of the agents employed, the relative percentage of active agents in the thermoplastic composition is selected to achieve the desired benefits. For example, active agents are typically employed in an amount of from about 1 wt. % to about 60 wt. %, in some embodiments from about 5 wt. % to about 50 wt. %, and in some embodiments, from about 10 wt. % to about 40 wt. %, based on the weight of the continuous phase (matrix polymer(s)). The concentration of agents relative to the entire thermoplastic composition may likewise be from about 0.5 wt. % to about 50 wt. %, in some embodiments from about 1 wt. % to about 30 wt. %, and in some embodiments, from about 2 wt. % to about 25 wt. %.

IV. Pore Initiation

As discussed above, the formation of a multimodal porous network in the polymeric material helps provide for the controlled release of the active agent over an extended period of time. To create the porous network, a deformational strain (e.g., bending, stretching, twisting, etc.) is applied, such as by straining in the longitudinal direction (e.g., machine direction), transverse direction (e.g., cross-machine direction), etc., as well as combinations thereof.

Straining may generally be performed manually (e.g., by a user) or using conventional equipment (e.g., mechanical drawing). One suitable mechanical drawing technique, for instance, is a nip roll process in which the material is passed between a nip defined between two rolls, at least one of which is rotatable. In one embodiment, at least one of the rolls contains a pattern of raised embossing elements, which can create a local deformation in the material. The other roll may likewise be patterned or smooth (e.g., anvil roll). If the deformed areas are stressed to a level above the cavitational yield stress, these areas can form initial pores. When subjected to further drawing stress, the pores areas will grow in size before the remaining material cavitates. Another suitable nip roll process involves the use of a grooved roll through which the polymeric material is able to course. Besides the use of a nip, the rotational velocity of the rolls themselves may also be utilized to help impart the desired degree of mechanical stress. In one embodiment, for example, the material is passed over a series of rolls that progressively draw the material. One such suitable method for accomplishing such drawing is through the use of a machine direction orienter ("MDO"). MDO units typically have a plurality of rolls (e.g., from 5 to 8) that can progressively draw and the polymeric material in the machine direction. The material may be drawn in either single or multiple discrete drawing operations. It should be noted that some of the rolls in an MDO apparatus may not be operating at progressively higher speeds. To draw the material in the manner described above, it is typically desired that the rolls of the MDO are not heated. Nevertheless, if desired, one or more rolls may be heated to a slight extent to facilitate the drawing process so long as the temperature of the composition remains below the ranges noted above.

Another example of a drawing technique is die drawing. In a typical die drawing process, the material is initially extruded into a precursor shape (e.g., profile) and quenched. The precursor is then mechanically drawn through a converging die while in a solid state. One particularly suitable die drawing process is pultrusion, during which the material is drawn or pulled through the die to form an engineered profile or shape determined by the shape of the die. Apart from die drawing, other mechanical drawing techniques may also be employed. In one embodiment, for instance, sheet drawing may be employed, such as tenter frame drawing, brake drawing, etc. In one particular embodiment, for instance, the polymeric material may be mechanically drawn in the form of a sheet using a mechanical, electrical, hydraulic or pneumatic brake assembly. The brake assembly may include a surface where the material is initially placed, a clamping bar, and a bending member that is lifted to create a bend in the material. More particularly, the brake assembly may include a plurality of generally c-shaped members that each present opposing clamping surfaces for receiving a polymeric material. Furthermore, a socket connection may be employed to rotatably support the bending member for bending the material disposed between the clamping surfaces. The socket connection generally includes a male portion and a female portion in sliding engagement with one another or connected by a pin hinge connection to one another. Such brake assemblies are known in the art and described in more detail in, for instance, U.S. Pat. No. 4,282,735 to Break; U.S. Pat. No. 4,557,132 to Break, and to U.S. Pat. No. 6,389,864 to Chubb.

Yet another technique involves the use of a fluidic medium (e.g., gas) to impart the desired degree of energy and stress to the material. One such process is, for instance, aspiration, which typically involves the use of blown air to draw the material. For example, a fiber draw aspirator may be employed, such as a linear fiber aspirator of the type shown in U.S. Pat. Nos. 3,802,817 and 3,423,255. A fiber draw aspirator generally includes an elongated vertical passage through which the fibers are drawn by aspirating air entering from the sides of the passage and flowing downwardly through the passage. A heater or blower may supply the aspirating air, which causes the fibers to draw or attenuate.

To perform the desired drawing, the thermoplastic composition may optionally be initially formed into a precursor, drawn, and thereafter converted into the desired polymeric material (e.g., films, fibers, webs, particles, etc.). The nature of the precursor is not critical, and it may be in the form of a sheet, film, web, fiber, profile, mold, bar, etc. Typically, the precursor has a thickness of from about 1 to about 5000 micrometers, in some embodiments from about 2 to about 4000 micrometers, in some embodiments from about 5 to about 2500 micrometers, and in some embodiments, from about 10 to about 500 micrometers. As an alternative to forming a precursor, the thermoplastic composition may also be drawn in situ as it is being shaped into the desired form (e.g., film or fiber) for the polymeric material.

Regardless of the technique employed, the degree of strain (e.g., in the machine direction) may be such that a draw ratio of from about 1.1 to about 3.5, in some embodiments from about 1.2 to about 3.0, and in some embodiments, from about 1.3 to about 2.5 is achieved. The draw ratio may be determined by dividing the length of the strained material by its length before straining. The rate may also vary to help achieve the desired properties, such as within the range of from about 5% to about 1500% per minute of deformation, in some embodiments from about 20% to about 1000% per minute of deformation, and in some embodiments, from about 25% to about 850% per minute of deformation. The material is generally kept at a temperature below the glass temperature of the matrix polymer and/or microinclusion additive during straining. Among other things, this helps to ensure that the polymer chains are not altered to such an extent that the porous network becomes unstable. For example, the material may be strained at a temperature that is at least about 10° C., in some embodiments at least about 20° C., and in some embodiments, at least about 30° C. below the glass transition temperature of the matrix polymer. For example, the material may be strained at a temperature of from about −50° C. to about 125° C., preferably from about −25° C. to about 100° C., and more preferably, from about −20° C. to about 50° C. In certain embodiments, straining may occur under ambient conditions, such as at a temperature of from about 0'C to about 50° C., in some embodiments from about 5° C. to about 40° C., and in some embodiments, from about 10° C. to about 35° C.

Straining in the manner described above can result in the formation of a porous network with the desired multimodal size distribution. Notably, the present inventors have discovered that this porous network can be effectively created before, during, and/or after incorporation of the active agent. For example, the active agent may be combined with the components of the thermoplastic composition prior to straining. In one embodiment, the active agent may be melt blended with the matrix polymer and inclusion additives in the manner described above and thereafter strained to create the porous network. The active agent may also be incorporated into the polymeric material after it is formed, but yet prior to straining. As an example, the polymeric material may be contacted with the active agent using conventional techniques, such as by impregnation, dipping, immersion into a bath, etc. Alternatively, the active agent may be applied to the polymeric material using a surface deposition technique, such as printing, coating, melt extruding, etc. Regardless, by incorporating the active agent into the material before it is strained, a substantial portion, if not all, of the active agent can be contained within the material before it is used. To create the porous network and allow the active agent to begin to release, the polymeric material can simply be strained (e.g., manually, such as by a user, with drawing equipment, etc.). Through this mechanism, the delivery system of the present invention can serve as a "user-activatable" system to deliver active agents when they are most needed and without substantial waste of material.

Of course, this is by no means a required feature of the present invention. In certain embodiments of the present invention, for instance, the active agent may be combined with the polymeric material during or after the porous network is created. In one embodiment, for instance, the material may be contacted (e.g., immersed in a bath) with the active agent as it is being strained. The polymeric material may also be applied with the active agent after the porous network is formed. In one embodiment, for instance, a fibrous web may be formed, strained to create a porous network, and thereafter contacted with the active agent, such as by impregnation, coating, etc. In yet other embodiments, a precursor may be initially formed and then strained to create a porous network, and thereafter, the strained precursor may be ground into particles. In such embodiments, the active agent can be contacted with the strained material before or after it is ground into particulate form.

V. Release Profile

Generally speaking, the active agent is capable of being controllably released from the polymeric material. The exact release profile depends in part on the size of the micropores and nanopores, which can be tuned by controlling the degree of strain and/or the temperature under which straining is performed, as discussed above. In certain circumstances, it may be desired to trigger the release of a portion of the active within a relatively short time. Such a "burst release" can, for example, be used to quickly reach a therapeutic amount of the active agent. Even after such a quick release, however, the unique nature of the porous network can allow the remaining portion of the active agent to be controllably released over an extended period of time to, for example, help maintain the agent at the therapeutic level. Various known mechanisms can be employed to trigger a burst release of the active agent, such as applying a liquid (e.g., solvent), pressure (e.g., pressing, rubbing, folding, etc.), heat, etc. In one embodiment, for instance, at least a portion of the polymeric material may be heated to a temperature at or above the glass transition temperature of the matrix polymer, such as at from about 40° to about 200° C., in some embodiments from about 50° C. to about 150° C., and in some embodiments, from about 70° C. to about 120° C. At such temperatures, the polymer will begin to flow and cause the pores to destabilize and collapse, which can cause a substantial portion of the active agent to quickly release from the material. It should also be understood that, although by no means required, a secondary encapsulation layer or material may be provided to help slow the release of the active agent until desired.

VI. Articles

Due to the unique ability to provide controlled release properties of an active agent, the polymeric material and delivery system of the present invention is well suited for use in a variety of different types of articles, such as absorbent articles, masks, creams, gels, lotions, ointments, oils, etc. For example, the polymeric material may be incorporated into an oil for delivering a chemically active agent, such as a viscosity modifier. In other embodiments, the polymeric material may be incorporated into an "absorbent article" for delivering a biologically active agent, such as an antimicrobial active. Absorbent articles are generally capable of absorbing water or other fluids and may include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth.

Materials and processes suitable for forming such articles are well known to those skilled in the art. Absorbent articles, for instance, typically include a substantially liquid-impermeable layer (e.g., outer cover), a liquid-permeable layer (e.g., topsheet, surge management layer, ventilation layer, wrap, etc.), and an absorbent core. The topsheet, for instance, is generally employed to help isolate the wearer's skin from liquids held in the absorbent core. Due to its proximity to the skin, a fibrous web is generally employed in the topsheet to provide a cloth-like feeling. If desired, the fibrous web used in the topsheet may be formed from the polymeric material of the present invention, which can be configured to release an active agent to a user's skin. The outer cover is likewise designed to be liquid-impermeable, but yet typically permeable to gases and water vapor (i.e., "breathable"). This permits vapors to escape from the absorbent core, but still prevents liquid exudates from passing through the outer cover. While the outer cover generally contains a film to impart the desired impermeability to liquids, a fibrous web is often laminated to the film as a facing to impart a more cloth-like feeling. If desired, the fibrous web used in the outer cover may be formed from the fibers of the present invention.

In yet another embodiment, the polymeric material of the present invention may be incorporated into a wipe configured for use on skin, such as a baby wipe, adult wipe, hand wipe, face wipe, cosmetic wipe, household wipe, industrial wipe, personal cleansing wipe, cotton ball, cotton-tipped swab, and so forth. The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. The wipe may be a "wet wipe" in that it contains a solution for cleaning, disinfecting, sanitizing, etc. The particular wet wipe solutions are not critical to the present invention and are described in more detail in U.S. Pat. No. 6,440,437 to Krzysik, et al.; U.S. Pat. No. 6,028,018 to Amundson, et al.; U.S. Pat. No. 5,888,524 to Cole; U.S. Pat. No. 5,667,635 to Win, et al.; U.S. Pat. No. 5,540,332 to Kopacz, et al.; and U.S. Pat. No. 4,741,944 to Jackson, et al.

The present invention may be better understood with reference to the following examples.

Test Methods

Film Tensile Properties:

Films may be tested for tensile properties (peak stress, modulus, strain at break, and energy per volume at break) on a MTS Synergie 200 tensile frame. The test may be performed in accordance with ASTM D638-10 (at about 23° C.). Film samples may be cut into dog bone shapes with a center width of 3.0 mm before testing. The dog-bone film samples may be held in place using grips on the MTS Synergie 200 device with a gauge length of 18.0 mm. The film samples may be stretched at a crosshead speed of 5.0 in/min until breakage occurred. Five samples may be tested for each film in both the machine direction (MD) and the cross direction (CD). A computer program (e.g., TestWorks 4) may be used to collect data during testing and to generate a stress versus strain curve from which a number of properties may be determined, including modulus, peak stress, elongation, and energy to break.

Melt Flow Rate:

The melt flow rate ("MFR") is the weight of a polymer (in grams) forced through an extrusion rheometer orifice (0.0825-inch diameter) when subjected to a load of 2160 grams in 10 minutes, typically at 190° C., 210° C., or 230° C. Unless otherwise indicated, melt flow rate is measured in accordance with ASTM Test Method D1239 with a Tinius Olsen Extrusion Plastometer.

Density and Percent Pore Volume:

To determine density and percent pore volume, the width ($W_i$) and thickness ($T_i$) of the specimen may be initially measured prior to straining. The length ($L_i$) before straining may also be determined by measuring the distance between two markings on a surface of the specimen. Thereafter, the specimen may be strained to initiate voiding. The width ($W_f$), thickness ($T_f$), and length ($L_f$) of the specimen may then be measured to the nearest 0.01 mm utilizing Digimatic Caliper (Mitutoyo Corporation). The volume ($V_i$) before straining may be calculated by $W_i \times T_i \times L_i = V_i$. The volume ($V_f$) after straining may also be calculated by $W_f \times T_f \times L_f = V_f$. The density ($P_f$) may be calculated by: $P_f = P_i/\phi$, where $P_i$ is density of precursor material, and the percent pore volume (% $V_v$) may be calculated by: % $V_v = (1 - 1/\phi) \times 100$.

Moisture Content:

Moisture content may be determined using an Arizona Instruments Computrac Vapor Pro moisture analyzer (Model No. 3100) in substantial accordance with ASTM D 7191-05, which is incorporated herein in its entirety by reference thereto for all purposes. The test temperature (§ X2.1.2) may be 130° C., the sample size (§ X2.1.1) may be 2 to 4 grams, and the vial purge time (§ X2.1.4) may be 30 seconds. Further, the ending criteria (§ X2.1.3) may be defined as a "prediction" mode, which means that the test is ended when the built-in programmed criteria (which mathematically calculates the end point moisture content) is satisfied.

Example 1

The ability to create a unique porous network within a polymeric material was demonstrated. Initially, a thermoplastic composition was formed from 85.3 wt. % polylactic acid (PLA 6201D, Natureworks®), 9.5 wt. % of a microinclusion additive, 1.4 wt. % of a nanoinclusion additive, and 3.8 wt. % of an internal interfacial modifier. The microinclusion additive was Vistamaxx™ 2120 (ExxonMobil), which is a polypropylene-polyethylene copolymer elastomer with a melt flow rate of 29 g/10 min (190° C., 2160 g) and a density of 0.866 g/cm³. The nanoinclusion additive was poly(ethylene-co-methyl acrylate-co-glycidyl methacrylate) (Lotader® AX8900, Arkema) having a melt flow rate of 5-6 g/10 min (190° C./2160 g), a glycidyl methacrylate content of 7 to 11 wt. %, methyl acrylate content of 13 to 17 wt. %, and ethylene content of 72 to 80 wt. %. The internal interfacial modifier was PLURIOL® WI 285 Lubricant from BASF, which is a polyalkylene glycol functional fluid.

The polymers were fed into a co-rotating, twin-screw extruder (ZSK-30, diameter of 30 mm, length of 1328 millimeters) for compounding that was manufactured by Werner and Pfleiderer Corporation of Ramsey, N.J. The extruder possessed 14 zones, numbered consecutively 1-14 from the feed hopper to the die. The first barrel zone #1 received the resins via gravimetric feeder at a total throughput of 15 pounds per hour. The PLURIOL® WI285 was added via injector pump into barrel zone #2. The die used to extrude the resin had 3 die openings (6 millimeters in diameter) that were separated by 4 millimeters. Upon formation, the extruded resin was cooled on a fan-cooled conveyor belt and formed into pellets by a Conair pelletizer. The extruder screw speed was 200 revolutions per minute ("rpm"). The pellets were then flood fed into an injection mold device (Spritzgiessautomaten BOY 22D) to form a tensile bar in accordance with ASTM D638 Type I. Temperature zones for the injection molding process ranged from 185° C. to 225° C., the holding pressure was 10 to 14 seconds, the cooling time was 25 to 50 seconds, the cycle time was 35 to 65 seconds, and the mold temperature was either about 10° C. or 21° C.

Figure 2:
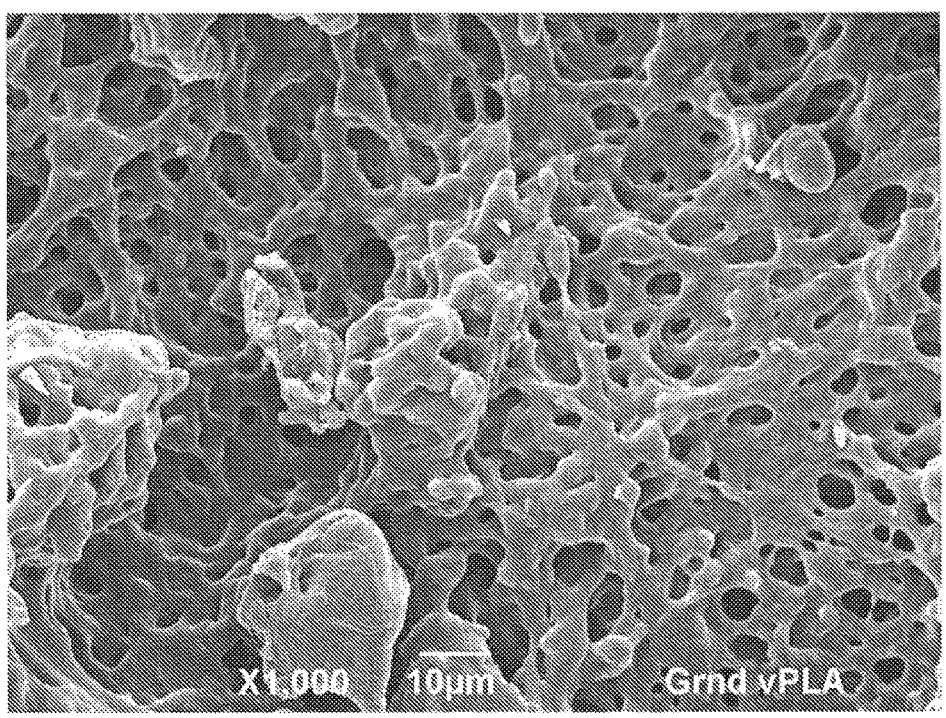

Once formed, the tensile bars were then drawn via a MTS 810 system at 23° C. (±3° C.) at a rate of 5 millimeters per minute and nominal length of 115 millimeters to a percent elongation of 54%. The expansion ratio, density, and void volume were determined to be 1.38, 0.86 g/cm³, and 27.5%, respectively. The voided material was then cut into about samples having a size of about 3 to 5 millimeters and cooled in liquid nitrogen for 15 minutes. Thereafter, the samples were applied to a Brinkman Retsch bench top pulverizer, which was set to speed 2. The morphology of the resulting particles was analyzed by scanning electron microscopy (SEM). The results are shown in FIGS. 1-2. As shown, the particles possessed a multimodal porous network having both micropores and nanopores.

Example 2

Figure 3:
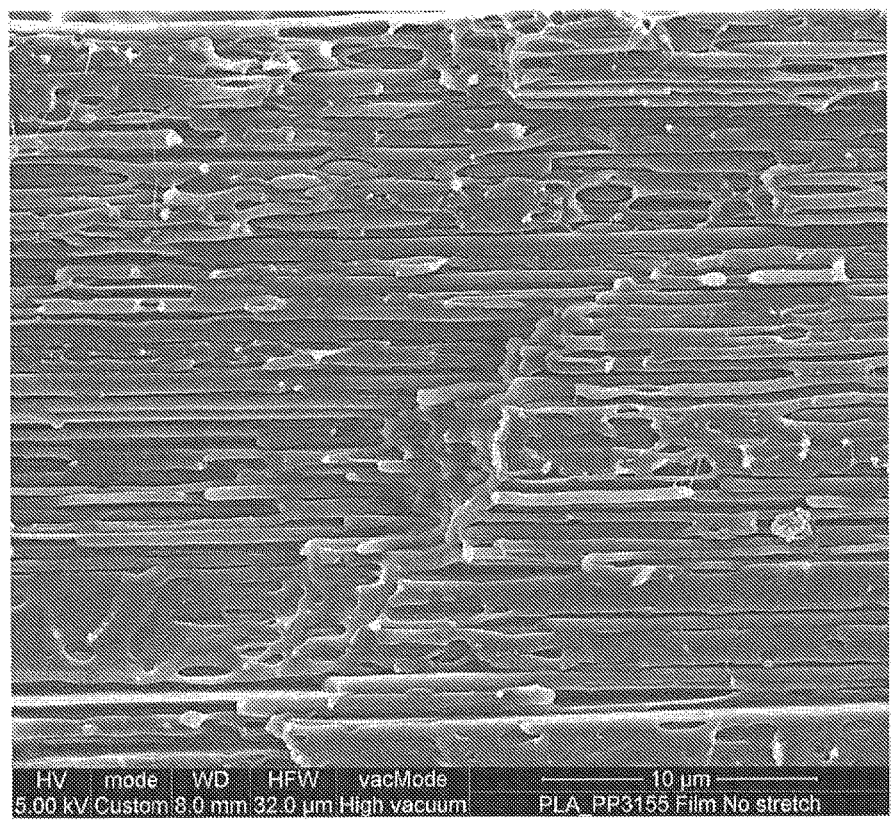
FIGS. 3-4 are SEM microphotographs of the unstretched film of Example 2, where the film was cut perpendicular to the machine direction in FIG. 3 and parallel to the machine direction in FIG. 4.
Figure 4:
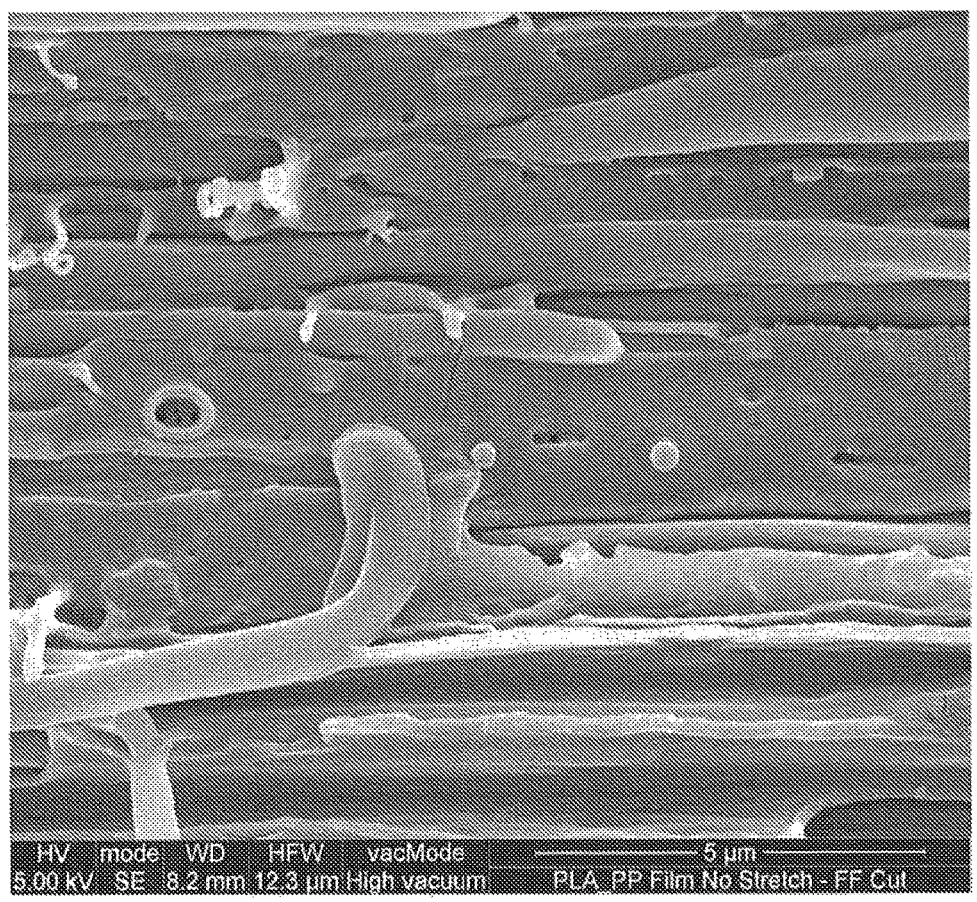
Figure 5:
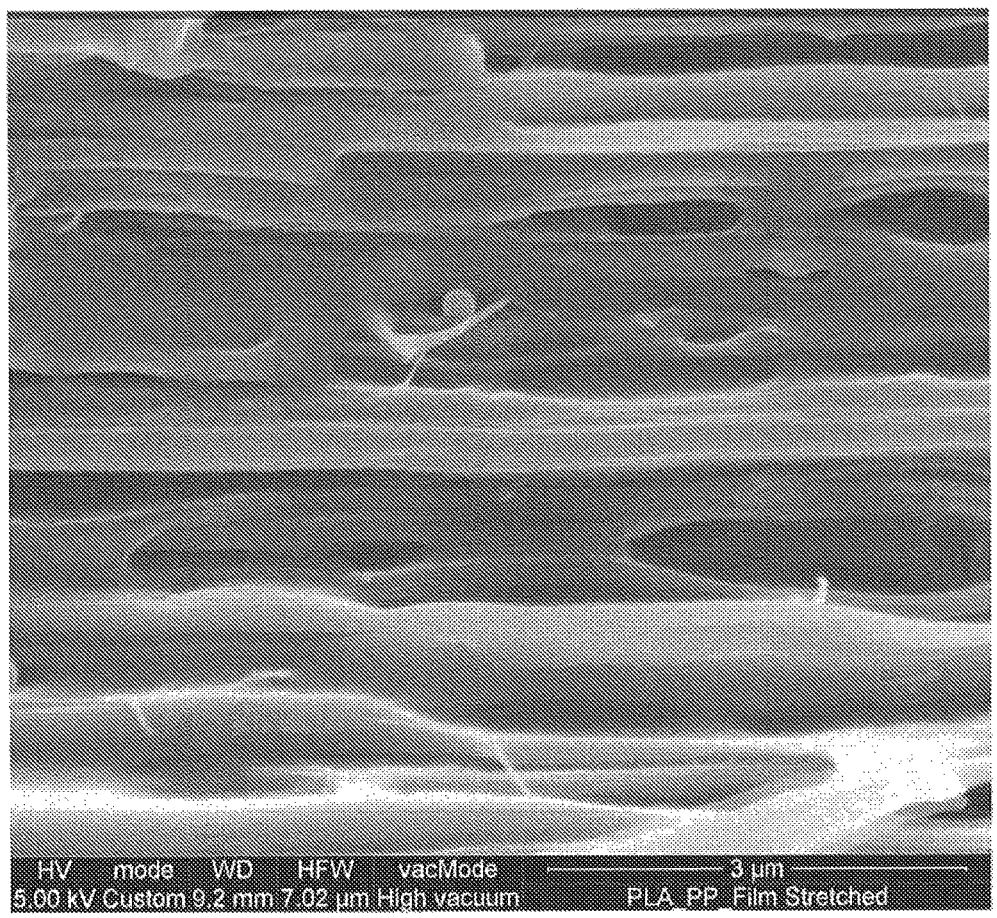
FIGS. 5-6 are SEM microphotographs of the stretched film of Example 2 (film was cut parallel to machine direction orientation).
Figure 6:
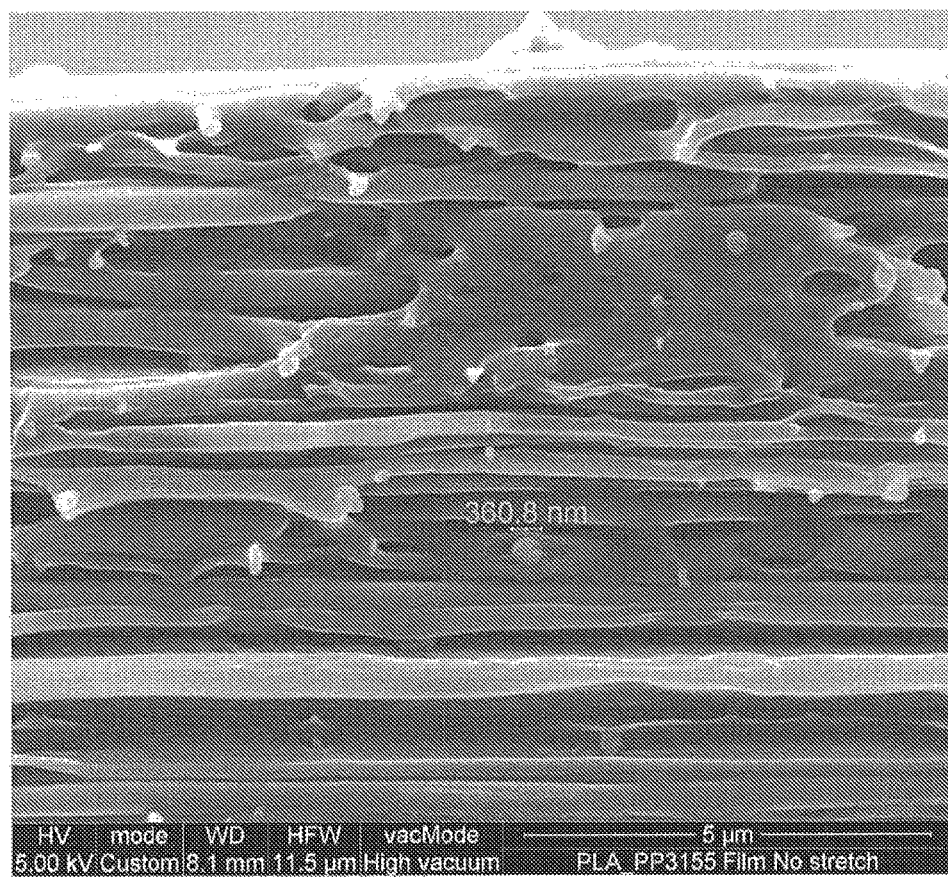

The ability to create a unique porous network within a polymeric material was demonstrated. Initially, pellets of a thermoplastic composition were formed as described in Example 1 and then flood fed into a signal screw extruder heated to a temperature of 212° C. where the molten blend exited through 4.5 inch width slit die and drawn to a film thickness ranging from 36 µm to 54 µm. The films were stretched in the machine direction to about 100% to initiate cavitation and void formation. The morphology of the films was analyzed by scanning electron microscopy (SEM) before and after stretching. The results are shown in FIGS. 3-6. As shown in FIGS. 3-4, the microinclusion additive was initially dispersed in domains having an axial size (in machine direction) of from about 2 to about 30 micrometers and a transverse dimension (in cross-machine direction) of from about 1 to about 3 micrometers, while the nanoinclusion additive was initially dispersed as spherical or spheroidal domains having an axial size of from about 100 to about 300 nanometers, FIGS. 5-6 show the film after stretching. As indicated, pores formed around the inclusion additives. The micropores formed around the microinclusion additive generally had an elongated or slit-like shape with a broad size distribution ranging from about 2 to about 20 micrometers in the axial direction. The nanopores associated with the nanoinclusion additive generally had a size of from about 50 to about 500 nanometers.

Example 3

The compounded pellets of Example 1 were dry blended with a third inclusion additive, which was a halloisite clay masterbatch (MacroComp MNH-731-36, MacroM) containing 22 wt. % of a styrenic copolymer modified nanoclay and 78 wt. % polypropylene (Exxon Mobil 3155). The mixing ratio was 90 wt. % of the pellets and 10 wt. % of the clay masterbatch, which provided a total clay content of 2.2%. The dry blend was then flood fed into a signal screw extruder heated to a temperature of 212° C., where the molten blend exited through 4.5 inch width slit die and drawn to a film thickness ranging from 51 to 58 µm. The films were stretched in the machine direction to about 100% to initiate cavitation and void formation.

Figure 7:
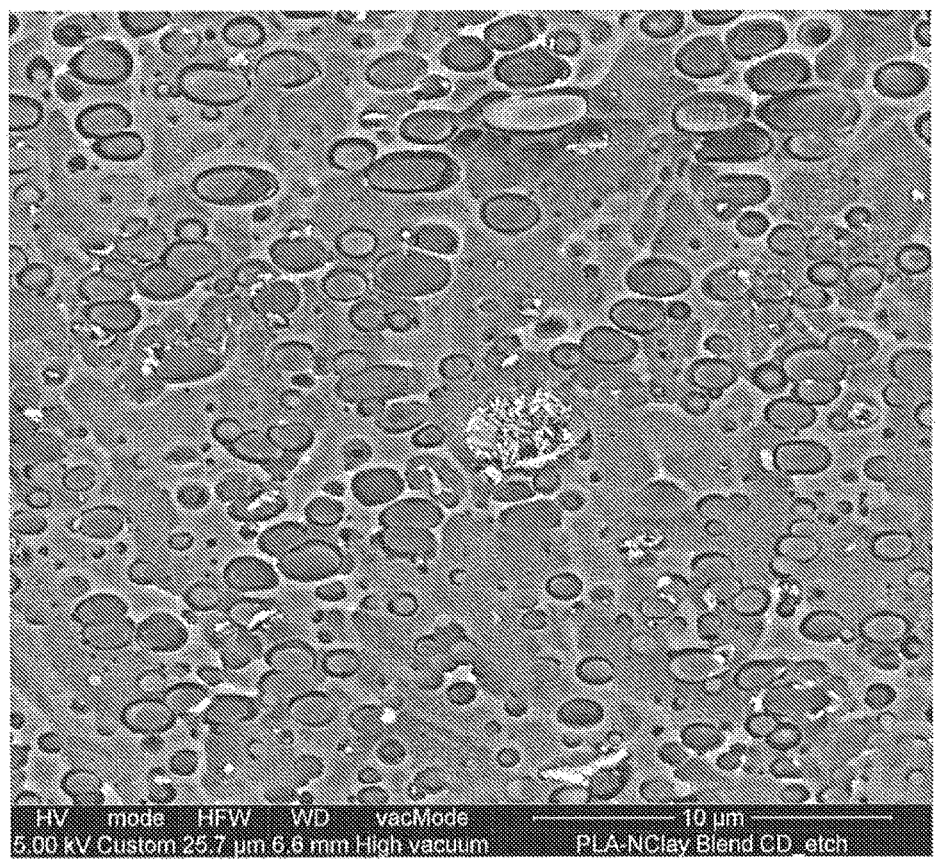
FIGS. 7-8 are SEM microphotographs of the unstretched film of Example 3, where the film was cut perpendicular to the machine direction in FIG. 7 and parallel to the machine direction in FIG. 8.
Figure 8:
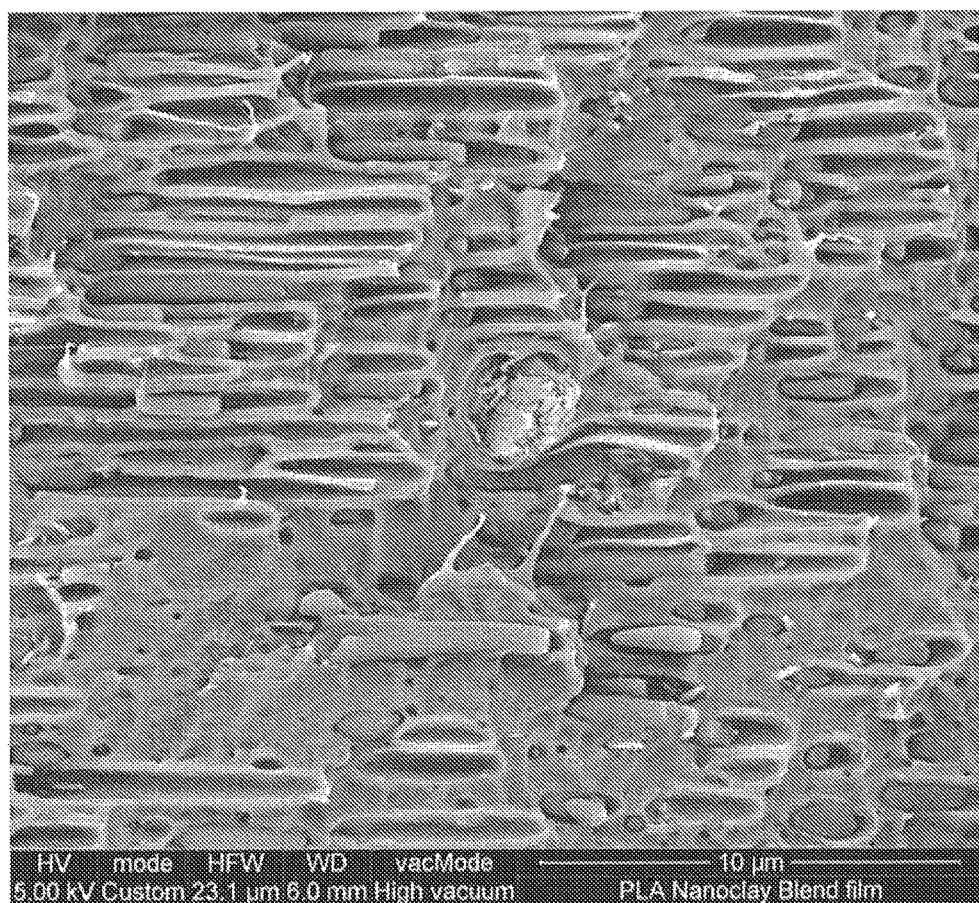
Figure 9:
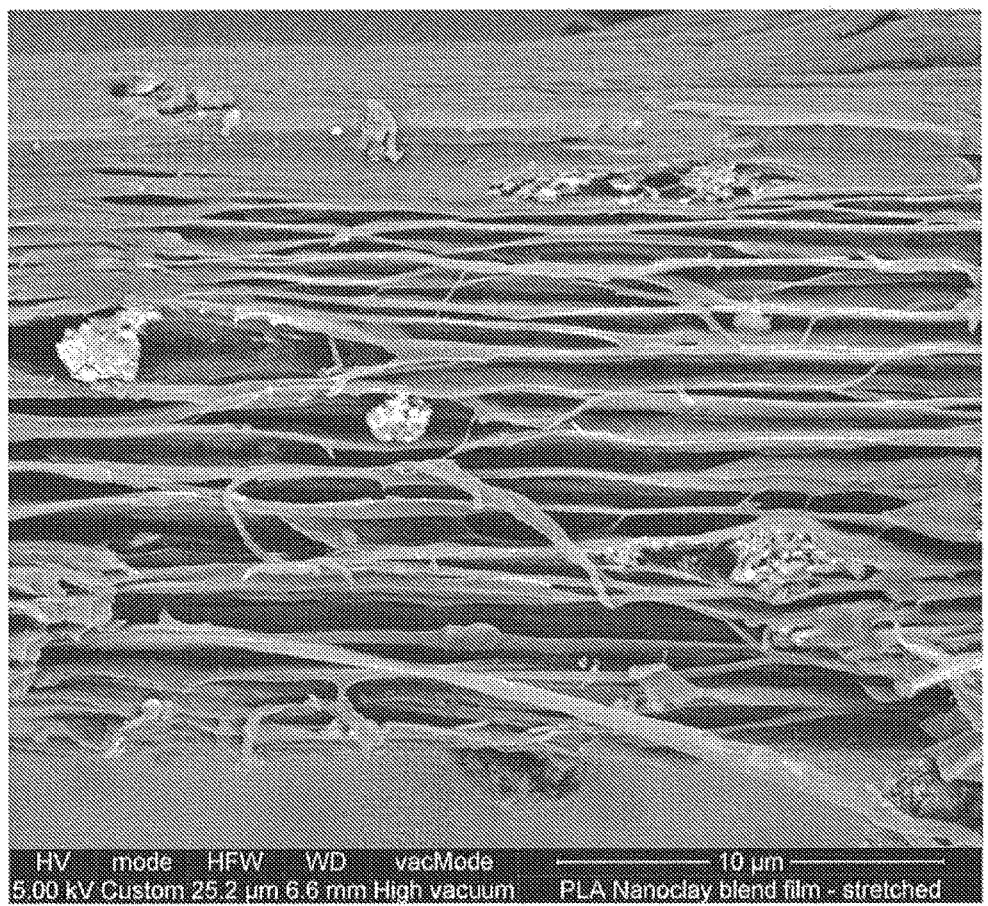
FIGS. 9-10 are SEM microphotographs of the stretched film of Example 3 (film was cut parallel to machine direction orientation).
Figure 10:
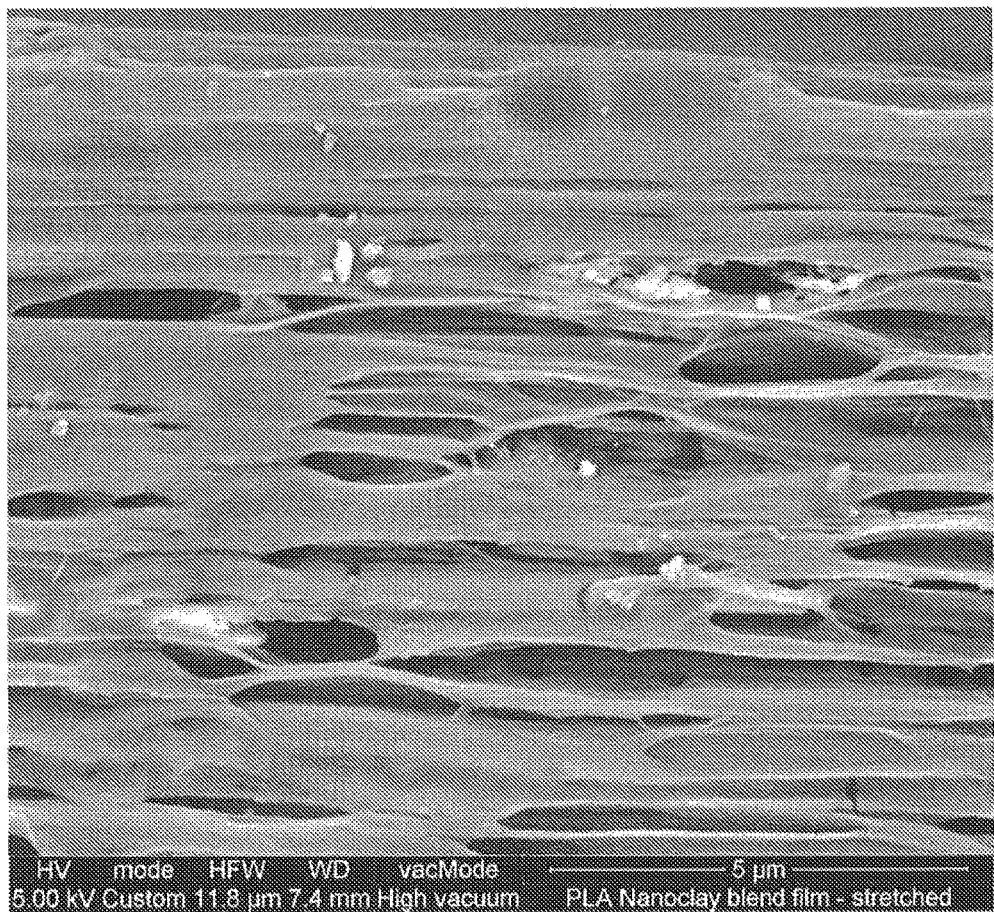

The morphology of the films was analyzed by scanning electron microscopy (SEM) before and after stretching. The results are shown in FIGS. 7-10. As shown in FIGS. 7-8, some of the nanoclay particles (visable as brighter regions) became dispersed in the form of very small domains—i.e., axial dimension ranging from about 50 to about 300 nanometers. The masterbatch itself also formed domains of a micro-scale size (axial dimension of from about 1 to about 5 micrometers). Also, the microinclusion additive (Vistamax™) formed elongated domains, while the nanoinclusion additive (Lotader®, visible as ultrafine dark dots) and the nanoclay masterbatch formed spheroidal domains. The stretched film is shown in FIGS. 9-10. As shown, the voided structure is more open and demonstrates a broad variety of pore sizes. In addition to highly elongated micropores formed by the first inclusions (Vistamaxx™), the nanoclay masterbatch inclusions formed more open spheroidal micropores with an axial size of about 10 microns or less and a transverse size of about 2 microns. Spherical nanopores are also formed by the second inclusion additive (Lotader®) and third inclusion additive (nanoclay particles).

Example 4

The ability to create a polymeric material having unique properties was demonstrated. Initially, a blend of 85.3 wt. % PLA 6201D, 9.5 wt. % of Vistamaxx™ 2120, 1.4 wt. % of Lotader® AX8900, and 3.8 wt. % of PLURIOL® WI 285 was formed. The polymers were fed into a co-rotating, twin-screw extruder (ZSK-30, diameter of 30 mm, length of 1328 millimeters) for compounding that was manufactured by Werner and Pfleiderer Corporation of Ramsey, N.J. The extruder possessed 14 zones, numbered consecutively 1-14 from the feed hopper to the die. The first barrel zone #1 received the resins via gravimetric feeder at a total throughput of 15 pounds per hour. The PLURIOL® WI285 was added via injector pump into barrel zone #2. The die used to extrude the resin had 3 die openings (6 millimeters in diameter) that were separated by 4 millimeters. Upon formation, the extruded resin was cooled on a fan-cooled conveyor belt and formed into pellets by a Conair pelletizer. The extruder screw speed was 200 revolutions per minute ("rpm"). The pellets were then flood fed into a signal screw extruder heated to a temperature of 212° C. where the molten blend exited through 4.5 inch width slit die and drawn to a film thickness ranging from 0.54 to 0.58 mm.

Example 5

Pellets were formed as described in Example 4 and then flood fed into a Rheomix 252 single screw extruder with a L/D ratio of 25:1 and heated to a temperature of 212° C. where the molten blend exited through a Haake 6 inch width s cast film die and drawn to a film thickness ranging from 39.4 µm to 50.8 µm via Haake take-up roll. The film was drawn in the machine direction to a longitudinal deformation of 160%/o at a pull rate of 50 mm/min (deformation rate of 67%/min) via MTS Synergie 200 tensile frame with grips at a gage length of 75 mm.

Example 6

Films were formed as described in Example 5, except that the film was also stretched in the cross-machine direction to a deformation of 100% at a pull rate of 50 mm/min (deformation rate of 100%/min) with grips at a gage length of 50 mm. Various properties of the films of Examples 5-6 were tested as described above. The results are set forth below in the tables below.

Film Properties

| Ex. | Average Thickness (µm) | Expansion Ratio (φ) | Percent Void Volume (% $V_v$) | Density (g/cm$^3$) |
|---|---|---|---|---|
| 5 | 41.4 | 1.82 | 45 | 0.65 |
| 6 | 34.0 | 2.13 | 53 | 0.56 |

Tensile Properties

| Example | | Avg. Thickness (µm) | Avg. Modulus (MPa) | Avg. Yield Stress (MPa) | Avg. Break Stress (MPa) | Avg. Strain at Break (%) | Avg. Energy per Volume at Break (J/cm$^3$) |
|---|---|---|---|---|---|---|---|
| 5 | MD | 44.5 | 466 | 41.4 | 36.9 | 54.6 | 16.8 |
|   | CD | 40.4 | 501 | 15.9 | 15.9 | 62.6 | 9.4 |
| 6 | MD | 37.3 | 265 | 26.7 | 26.3 | 85.5 | 15.8 |
|   | CD | 34.3 | 386 | 25.1 | 25.2 | 45.8 | 9.3 |

Example 7

The ability to form a polymeric material having unique properties was demonstrated. Initially, pellets of a thermoplastic composition were formed as described in Example 1 and then flood fed into a single screw extruder at 240° C., melted and passed through a melt pump at a rate of 0.40 grams per hole per minute through a 0.6 mm diameter spinneret. Fibers were collected in free fall (gravity only as draw force). Fibers were then cold drawn at 23° C. in a MTS Synergie Tensile frame at a rate of 50 mm/min. Fibers were drawn to pre-defined strains of 50%, 100%, 150%, 200% and 250%. After drawing, the expansion ratio, void volume and density were calculated for various strain rates as shown in the tables below.

| Initial Length (mm) | Initial Diameter (mm) | Initial Volume (mm^3) | Strain % | Length after elongation (mm) | Diameter after elongation (mm) | Volume after elongation (mm^3) |
|---|---|---|---|---|---|---|
| 50 | 0.1784 | 1.2498 | 50.0 | 75 | 0.1811 | 1.9319 |
| 50 | 0.2047 | 1.6455 | 100.0 | 100 | 0.2051 | 3.3039 |
| 50 | 0.1691 | 1.1229 | 150.0 | 125 | 0.165 | 2.6728 |
| 50 | 0.242 | 2.2998 | 200.0 | 150 | 0.1448 | 2.4701 |
| 50 | 0.1795 | 1.2653 | 250.0 | 175 | 0.1062 | 1.5502 |

| Strain % | Expansion Ratio | Void Volume (%) | Initial Density (g/cc) | Voided Density (g/cc) |
|---|---|---|---|---|
| 50 | 1.55 | 35.3 | 1.2 | 0.78 |
| 100 | 2.01 | 50.2 | 1.2 | 0.60 |
| 125 | 2.38 | 58.0 | 1.2 | 0.50 |
| 150 | 1.07 | 6.9 | 1.2 | 1.12 |
| 175 | 1.23 | 18.4 | 1.2 | 0.98 |

Example 8

Fibers were formed as described in Example 7, except that they were collected at a collection roll speed of 100 meters per minute resulting in a drawn down ratio of 77. Fibers were then cold drawn at 23° C. in a MTS Synergie Tensile frame at a rate of 50 mm/min. Fibers were drawn to pre-defined strains of 50%, 100%, 150%, 200% and 250%. After drawing, the expansion ratio, void volume and density were calculated for various strain rates as shown in the tables below.

| Initial Length (mm) | Initial Diameter (mm) | Initial Volume (mm^3) | Strain % | Length after elongation (mm) | Diameter after elongation (mm) | Volume after elongation (mm^3) |
|---|---|---|---|---|---|---|
| 50 | 0.057 | 0.1276 | 50.0 | 75 | 0.0575 | 0.1948 |
| 50 | 0.0601 | 0.1418 | 100.0 | 100 | 0.0609 | 0.2913 |
| 50 | 0.067 | 0.1763 | 150.0 | 125 | 0.0653 | 0.4186 |
| 50 | 0.0601 | 0.1418 | 200.0 | 150 | 0.058 | 0.3963 |
| 50 | 0.0601 | 0.1418 | 200.0 | 150 | 0.0363 | 0.1552 |
| 50 | 0.059 | 0.1367 | 250.0 | 175 | 0.0385 | 0.2037 |

| Strain % | Expansion Ratio | Void Volume (%) | Initial Density (g/cc) | Voided Density (g/cc) |
|---|---|---|---|---|
| 50 | 1.53 | 34.5 | 1.2 | 0.79 |
| 100 | 2.05 | 51.3 | 1.2 | 0.58 |
| 150 | 2.37 | 57.9 | 1.2 | 0.51 |
| 200 | 2.79 | 64.2 | 1.2 | 0.43 |
| 200 | 1.09 | 8.6 | 1.2 | 1.10 |
| 250 | 1.49 | 32.9 | 1.2 | 0.81 |

Example 9

Fibers were formed as described in Example 7, except that the blend was composed of 83.7 wt. % polylactic acid (PLA 6201D, Natureworks®), 9.3 wt. % of Vistamaxx™ 2120, 1.4 wt. % Lotader® AX8900, 3.7% wt. % PLURIOL® WI 285, and 1.9% hydrophilic surfactant (Masil SF-19). The PLURIOL® WI285 and Masil SF-19 were premixed at a 2:1 (WI-285:SF-19) ratio and added via injector pump into barrel zone #2. Fibers were collected at 240° C., 0.40 ghm and under free fall.

Example 10

Fibers were formed as described in Example 9, except that they were collected at a collection roll speed of 100 meters per minute resulting in a drawn down ratio of 77. Fibers were then cold drawn at 23° C. in a MTS Synergie Tensile frame at a rate of 50 mm/min. Fibers were drawn to pre-defined strain of 100%. After drawing, the expansion ratio, void volume and density were calculated as shown in the tables below.

| Example | Initial Length (mm) | Initial Diameter (mm) | Initial Volume (mm^3) | Strain % | Length after elongation (mm) | Diameter after elongation (mm) | Volume after elongation (mm^3) |
|---|---|---|---|---|---|---|---|
| 10 | 50 | 0.0626 | 0.1539 | 100.0 | 100 | 0.0493 | 0.1909 |

| Example | Expansion Ratio | Void Volume (%) | Initial Density (g/cm³) | Voided Density (g/cm³) |
|---|---|---|---|---|
| 10 | 1.24 | 19.4 | 1.2 | 0.97 |

Example 11

Fibers from Example 8 were stretched in a MTS Synergie Tensile frame at a rate of 50 millimeters per minute to 250% strain. This opened up the void structure and turned the fiber white. A one inch sample was then cut from the stressed, white area of the fiber. The new fiber was then tested as described above. The density was estimated to be 0.75 grams per cubic centimeters and the pull rate for the tensile test was 305 mm/min.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A delivery system comprising an active agent that is contained within a polymeric material,
   wherein the polymeric material is formed from a thermoplastic composition containing a continuous phase that includes a matrix polymer,
   wherein a microinclusion additive and nanoinclusion additive are dispersed within the continuous phase in the form of discrete domains, and
   wherein the microinclusion additive is present in the thermoplastic composition in an amount of from 0.1 wt. % to 20 wt. % and the nanoinclusion additive is present in the thermoplastic composition in an amount of from 0.01 wt. % to 15 wt. %, and
   wherein a porous network is defined in the polymeric material that contains a plurality of nanopores and micropores.

2. The delivery system of claim 1, wherein the micropores have an average cross-sectional dimension of from about 0.5 to about 30 micrometers.

3. The delivery system of claim 1, wherein the nanopores have an average cross-sectional dimension of from about 1 to about 500 nanometers.

4. The delivery system of any of claim 1, wherein the average pore volume of the material is from about 15% to about 80% per cm³.

5. The delivery system of any of claim 1, wherein the nanopores constitute about 20 vol. % or more of the total pore volume of the material.

6. The delivery system of claim 1, wherein the continuous phase constitutes from about 60 wt. % to about 99 wt. % of the thermoplastic composition.

7. The delivery system of claim 1, wherein the matrix polymer includes a polyester having a glass transition temperature of about 0° C. or more.

8. The delivery system of claim 7, wherein the polyester includes polylactic acid.

9. The delivery system of claim 1, wherein the microinclusion additive is polymeric.

10. The delivery system of claim 1, wherein the ratio of the solubility parameter for the matrix polymer to the solubility parameter of the microinclusion additive is from about 0.5 to about 1.5, the ratio of the melt flow rate for the matrix polymer to the melt flow rate of the microinclusion additive is from about 0.2 to about 8, and/or the ratio of the Young's modulus elasticity of the matrix polymer to the Young's modulus of elasticity of the microinclusion additive is from about 1 to about 250.

11. The delivery system of claim 1, wherein the nanoinclusion additive is polymeric.

12. The delivery system of claim 11, wherein the nanoinclusion additive is a polyepoxide.

13. The delivery system of claim 1, wherein the microinclusion additive constitutes from 1 wt. % to 20 wt. % of the composition, based on the weight of the continuous phase and/or the nanoinclusion additive constitutes from 0.05 wt. % to 10 wt. % of the composition, based on the weight of the continuous phase.

14. The delivery system of claim 1, wherein the thermoplastic composition further comprises an interphase modifier.

15. The delivery system of claim 1, wherein the polymeric material is in the form of a film, fibers, fibrous web, particles, or a combination thereof.

16. The delivery system of any of claim 1, wherein the active agent is a biologically active agent.

17. An absorbent article comprising the delivery system of claim 1.

18. A delivery system comprising an active agent that is contained within a polymeric material,
   wherein the polymeric material is formed from a thermoplastic composition containing a continuous phase that includes a matrix polymer,
   wherein a microinclusion additive and nanoinclusion additive are dispersed within the continuous phase in the form of discrete domains,
   wherein the microinclusion additive is present in the thermoplastic composition in an amount of from 0.1 wt. % to 20 wt. % and the nanoinclusion additive is present in the thermoplastic composition in an amount of from 0.01 wt. % to 15 wt. %, and
   wherein the ratio of the solubility parameter for the matrix polymer to the solubility parameter of the microinclusion additive is from about 0.5 to about 1.5, the ratio of the melt flow rate for the matrix polymer to the melt flow rate of the microinclusion additive is from about 0.2 to about 8, and/or the ratio of the Young's modulus elasticity of the matrix polymer to the Young's modulus of elasticity of the microinclusion additive is from about 1 to about 250.

19. A method for forming a delivery system for an active agent, the method comprising:
   melt blending a matrix polymer, microinclusion additive, nanoinclusion additive, and active agent to form a thermoplastic composition that contains a continuous phase that includes the matrix polymer and within which is dispersed discrete domains of the microinclusion additive and the nanoinclusion additive,
   wherein the microinclusion additive is present in the thermoplastic composition in an amount of from 0.1 wt. % to 20 wt. % and the nanoinclusion additive is present in the thermoplastic composition in an amount of from 0.01 wt. % to 15 wt. %;
   forming a polymeric material from the thermoplastic composition; and
   straining the polymeric material to achieve a porous network that contains a plurality of nanopores and micropores.

20. A method for forming a delivery system for an active agent, the method comprising:

melt blending a matrix polymer, microinclusion additive, and nanoinclusion additive to form a thermoplastic composition that contains a continuous phase that includes the matrix polymer and within which is dispersed discrete domains of the microinclusion additive and the nanoinclusion additive, wherein the microinclusion additive is present in the thermoplastic composition in an amount of from 0.1 wt. % to 20 wt. % and the nanoinclusion additive is present in the thermoplastic composition in an amount of from 0.01 wt. % to 15 wt. %;

forming a polymeric material from the thermoplastic composition;

straining the polymeric material to achieve a porous network that contains a plurality of nanopores and micropores; and contacting the polymeric material with the active agent before, during, and/or after straining.

* * * * *